United States Patent
Vianello et al.

(10) Patent No.: US 7,101,876 B2
(45) Date of Patent: *Sep. 5, 2006

(54) SUBSTITUTED BENZOXAZINES AS INTEGRIN ANTAGONISTS

(75) Inventors: Paola Vianello, Milan (IT); Tiziano Bandiera, Gambolò (IT)

(73) Assignee: Pharmacia Corporation, NJ (US)

( * ) Notice: Subject to any disclaimer, the term of this patent is extended or adjusted under 35 U.S.C. 154(b) by 117 days.

This patent is subject to a terminal disclaimer.

(21) Appl. No.: 10/821,104

(22) Filed: Apr. 8, 2004

(65) Prior Publication Data

US 2004/0224948 A1 Nov. 11, 2004

Related U.S. Application Data

(63) Continuation of application No. 09/924,709, filed on Aug. 8, 2001, now Pat. No. 6,750,215.

(51) Int. Cl.
- C07D 265/36 (2006.01)
- C07D 413/12 (2006.01)
- A61K 31/536 (2006.01)
- A61P 35/04 (2006.01)

(52) U.S. Cl. ................................ 514/230.5; 544/105
(58) Field of Classification Search ............. 514/230.5; 544/105
See application file for complete search history.

(56) References Cited

U.S. PATENT DOCUMENTS 6,750,215 B1 * 6/2004 Vianello et al. ......... 514/230.5

FOREIGN PATENT DOCUMENTS

| WO | WO 00/39103 | 7/1999 |
| WO | WO 99/50257 | 6/2000 |

OTHER PUBLICATIONS

Montgomery et al., *Proc. Natl. Acad. Sci.* USA, vol. 91, pp. 8856-8860, Sep. 1994.
Seftor, et al., *Proc. Natl. Acad. Sci.* USA, vol. 89, pp. 1557-1561, Mar. 1992.
Adamis, et al., *Amer. J. Opthal.*, vol. 118, p. 445-450, Oct. 1994.
Peacock, et. al., *J. Exp. Med.*, J. Exp. Med., vol. 175, p. 1135-1138, Apr. 1992.
Brooks, et al., *Cell*, vol. 79, pp. 1157-1164, Dec. 1994.
Brooks, et al., *Science*, vol. 264, pp. 569-571, Apr. 1994.
Sato, et al., *J. Cell Biol.*, vol. 111, pp. 1713-1723, Oct. 1990.
Fisher, et al., *Endocrinology*, vol. 132(3), pp. 1411-1413, 1993.
Choi, et al., *J. Vasc. Surg.*, vol. 19(1), pp. 125-134, Jan. 1994.
White, J.M., *Current Biology*, vol. 3(9), pp. 596-599, 1993.
Verlag, *Methods of Organic Chemistry* (Houben-Weil), vol. E 9a, pp. 141-177, Stuttgart 1997.
Krchnak, V., Flegelova, Z., Weichsel, A.S., Lebl, M., *Tetrahedron Letters*, vol. 36(35), pp. 6193-6196, 1995.
Brown, R.F.C., Jackson, W.R., McCarthy, T.D., *Tetrahedron*, vol. 50(18), pp. 5469-5488, 1994.
Beier, C., Schaumann, E., *Synthesis*, vol. 11, pp. 1296-1300, Jul. 1997.
Hinterberger, S., Hofer, O., Greger, H., *Tetrahedroni*, vol. 54, pp. 487-496, 1998.
Van Heerden, P.S., Bezuidenhoudt, B.C.B., Ferreira, D., *Tetrahedron* 1996, 52, 12313-12322.
Van Heerden, P.S., Bezuidenhoudt, B.C.B., Ferreira, D., *J. Chem. Soc. Perk. Trans. 1*, 1997, 1141-1146.
Greene, T.W., Wuts, P.G.M., *Protective Groups in Organic Synthesis*, Wiley, 1999.
Miller, W.H. et al., *Bioorg. Med. Chem. Lett.*, vol. 9, pp. 1807-1812, 1999.
Erez, M., et al., *J. Med. Chem.* 1978, 21, 982-984.
Young, R.N., Gauthier, J.Y., Coombs, W., *Tetrahedron Lett.*, vol. 25(17), pp. 1753-1756, 1984.
Yadagiri, B. Lown, J.W., *Synthetic Communications*, vol. 20(2), pp. 175-181, 1990.
Wong, et al., *Molecular Pharmacology* 50:529-537, 1996.
Pytela, et al., *Methods in Enzymology*, vol. 144, pp. 475-489, 1987.
Berryman, et al., *Chemical Abstracts*, vol. 131:257572, 1999.

* cited by examiner

*Primary Examiner*—Kahsay Habte
(74) *Attorney, Agent, or Firm*—Matthew J. Pugmire; Bryan C. Zielinski

(57) ABSTRACT

The present invention relates to a class of compounds represented by the formula (I)

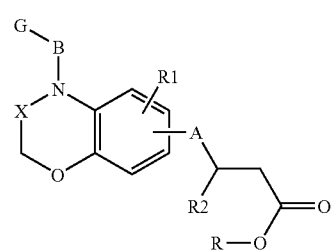

I or a pharmaceutical acceptable salt, prodrug or ester thereof, pharmaceutical compositions comprising compounds of the formula (I), and methods of selectively inhibiting or antagonizing $\alpha_v\beta_3$ integrin.

4 Claims, No Drawings

SUBSTITUTED BENZOXAZINES AS INTEGRIN ANTAGONISTS

This application is a continuation of U.S. application Ser. No. 09/924,709 filed Aug. 8, 2001, now U.S. Pat. No. 6,750,215.

FIELD OF THE INVENTION

The present invention relates to novel compounds which bind to the integrin receptor $\alpha_v\beta_3$, to pharmaceutical compositions containing such compounds, processes for preparing such compounds, and to methods of using these compounds, alone or in combination with other therapeutic agents.

BACKGROUND OF THE INVENTION

Integrins are a group of cell surface glycoproteins which mediate cell adhesion and therefore are useful mediators of cell adhesion interactions which occur during various biological processes. Integrins are heterodimers composed of noncovalently linked $\alpha$ and $\beta$ polypeptide subunits. Currently eleven different $\alpha$ subunits have been identified and six different $\beta$ subunits have been identified. The various a subunits can combine with various $\beta$ subunits to form distinct integrins.

The integrin identified as $\alpha_v\beta_3$ (also known as the vitronectin receptor) has been identified as an integrin which plays a role in various conditions or disease states including tumor metastasis, solid tumor growth (neoplasia), osteoporosis, Paget's disease, humoral hypercalcemia of malignancy, angiogenesis, including tumor angiogenesis, retinopathy including macular degeneration, arthritis, including rheumatoid arthritis, periodontal disease, psoriasis and smooth muscle cell migration (e.g. restenosis artherosclerosis). Additionally, it has been found that such agents would be useful as antivirals, antifungals and antimicrobials. Thus, compounds which selectively inhibit or antagonize $\alpha_v\beta_3$ would be beneficial for treating such conditions.

It has been shown that the $\alpha_v\beta_3$ integrin and other $\alpha_v$ containing integrins bind to a number of Arg-Gly-Asp (RGD) containing matrix macromolecules. Compounds containing the RGD sequence mimic extracellular matrix ligands so as to bind to cell surface receptors. However, it is also known that RGD peptides in general are non-selective for RGD dependent integrins. For example, most RGD peptides which bind to $\alpha_v\beta_3$ also bind to $\alpha_v\beta_5$, $\alpha_v\beta_1$ and $\alpha_{IIb}\beta_3$. Antagonism of platelet $\alpha_{IIb}\beta_3$ (also known as the fibrinogen receptor) is known to block platelet aggregation in humans. In order to avoid bleeding side-effects when treating the conditions or disease states associated with the integrin $\alpha_v\beta_3$, it would be beneficial to develop compounds which are selective antagonists of $\alpha_v\beta_3$ as opposed to $\alpha_{IIb}\beta_3$.

The compounds of this invention are therefore selective $\alpha_v\beta_3$ integrin antagonist. The present invention includes compounds which inhibit the respective integrins and also includes pharmaceutical compositions comprising such compounds. The present invention further provides for methods for treating or preventing conditions mediated by the $\alpha_v\beta_3$ receptor in a mammal in need of such treatment comprising administering a therapeutically effective amount of the compounds of the present invention and pharmaceutical compositions of the present invention. Administration of such compounds and compositions of the present invention inhibits angiogenesis, tumor metastasis, tumor growth, osteoporosis, Paget's disease, humoral hypercalcemia of malignancy, retinopathy, macular degeneration, arthritis, periodontal disease, smooth muscle cell migration, including restenosis and artherosclerosis, and viral diseases.

Tumor cell invasion occurs by a three step process: 1) tumor cell attachment to extracellular matrix; 2) proteolytic dissolution of the matrix; and 3) movement of the cells through the dissolved barrier. This process can occur repeatedly and can result in metastases at sites distant from the original tumor.

Seftor et al. (Proc. Natl. Acad. Sci. USA, Vol. 89 (1992) 1557–1561) have shown that the $\alpha_v\beta_3$ integrin has a biological function in melanoma cell invasion. Montgomery et al., (Proc. Natl. Acad. Sci. USA, Vol. 91 (1994) 8856–60) have demonstrated that the integrin $\alpha_v\beta_3$ expressed on human melanoma cells promotes a survival signal, protecting the cells from apoptosis. Mediation of the tumor cell metastatic pathway by interference with the $\alpha_v\beta_3$ integrin cell adhesion receptor to impede tumor metastasis would be beneficial.

Brooks et al. (Cell, Vol. 79 (1994) 1157–1164) have demonstrated that antagonists of $\alpha_v\beta_3$ provide a therapeutic approach for the treatment of neoplasia (inhibition of solid tumor growth) since systemic administration of $\alpha_v\beta_3$ antagonists causes dramatic regression of various histologically distinct human tumors.

The adhesion receptor integrin $\alpha_v\beta_3$ was identified as a marker of angiogenic blood vessels in chick and man and therefore such receptor plays a critical role in angiogenesis or neovascularization. Angiogenesis is characterized by the invasion, migration and proliferation of smooth muscle and endothelial cells. Antagonists of $\alpha_v\beta_3$ inhibit this process by selectively promoting apoptosis of cells in neovasculature. The growth of new blood vessels, or angiogenesis, also contributes to pathological conditions such as diabetic retinopathy including macular degeneration (Adamis et al., Amer. J. Ophthal., Vol. 118, (1994) 445–450) and rheumatoid arthritis (Peacock et al., J. Exp. Med., Vol. 175, (1992), 1135–1138). Therefore, $\alpha_v\beta_3$ antagonists would be useful therapeutic agents for treating such conditions associated with neovascularization (Brooks et al., Science, Vol. 264, (1994), 569–571).

It has been reported that the cell surface receptor $\alpha_v\beta_3$ is the major integrin on osteoclasts responsible for attachment to bone. Osteoclasts cause bone resorption and when such bone resorbing activity exceeds bone forming activity it results in osteoporosis (loss of bone), which leads to an increased number of bone fractures, incapacitation and increased mortality. Antagonists of $\alpha_v\beta_3$ have been shown to be potent inhibitors of osteoclastic activity both in vitro [Sato et al., J. Cell. Biol., Vol. 111 (1990) 1713–1723] and in vivo [Fisher et al., Endocrinology, Vol. 132 (1993) 1411–1413]. Antagonism of $\alpha_v\beta_3$ leads to decreased bone resorption and therefore restores a normal balance of bone forming and resorbing activity. Thus it would be beneficial to provide antagonists of osteoclast $\alpha_v\beta_3$ which are effective inhibitors of bone resorption and therefore are useful in the treatment or prevention of osteoporosis.

The role of the $\alpha_v\beta_3$ integrin in smooth muscle cell migration also makes it a therapeutic target for prevention or inhibition of neointimal hyperplasia which is a leading cause of restenosis after vascular procedures (Choi et al., J. Vasc. Surg. Vol. 19(1) (1994) 125–34). Prevention or inhibition of neointimal hyperplasia by pharmaceutical agents to prevent or inhibit restenosis would be beneficial.

White (Current Biology, Vol. 3(9)(1993) 596–599) has reported that adenovirus uses $\alpha_v\beta_3$ for entering host cells. The integrin appears to be required for endocytosis of the virus particle and may be required for penetration of the viral genome into the host cell cytoplasm. Thus compounds which inhibit $\alpha_v\beta_3$ would find usefulness as antiviral agents.

SUMMARY OF THE INVENTION

The present invention as a first object provides novel compounds of the following formula (I)

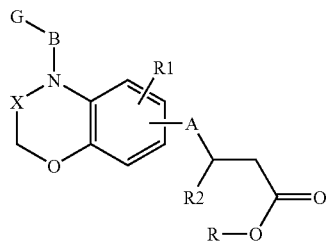

or a pharmaceutically acceptable salt, prodrug or ester thereof, wherein:
G is selected from the group consisting of a)

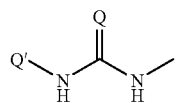

wherein Q is NH or O and Q' is H, $C_1$–$C_6$ alkyl, phenyl, or phenyl-$C_1$–$C_4$-alkyl;

b)

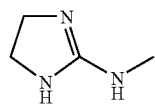

c)

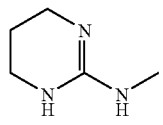

d)

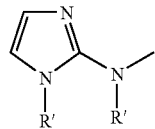

e)

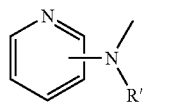

f)

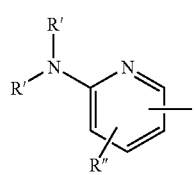

g)

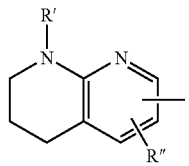

wherein R' and R" are independently H or $C_1$–$C_4$ alkyl;
B is $(CH_2)_m(CH=CH)_pY$, wherein m=1,2,3, p=0,1, Y is $CH_2$ or CO.
X is $CH_2$ or C=O;
R1 is selected from the group consisting of H, $C_1$–$C_4$ alkyl, $C_1$–$C_4$ alkoxy, OH, halogen, $CF_3$;
A is $CH_2$, NH, O, $S(O)_n$ wherein n is zero, 1 or 2.
R2 is $C_1$–$C_6$ alkyl, $C_2$–$C_6$ alkenyl, $C_2$–$C_6$ alkynyl, aryl or $C_5$–$C_7$ monocyclic heteroaryl ring containing one to three heteroatoms selected from O, S, and N, unsubstituted or optionally substituted by one to three substituents independently selected from H, $C_1$–$C_4$ alkyl, $C_1$–$C_4$ alkoxy, OH, halogen, $CF_3$;
R is hydrogen, $C_1$–$C_6$ alkyl, $C_2$–$C_6$ alkenyl, $C_2$–$C_4$ alkynyl, aryl or aryl-$C_1$–$C_4$ alkyl.

The present invention includes within its scope all possible isomers, stereoisomers and optical isomers and their mixtures, the chemical and bioprecursors and metabolites of the compounds of formula (I).

It is another object of the invention to provide pharmaceutical compositions comprising compounds of the Formula I. Such compounds and compositions are useful in selectively inhibiting or antagonizing the $\alpha_v\beta_3$ integrin and therefore in another embodiment the present invention relates to a method of selectively inhibiting or antagonizing the $\alpha_v\beta_3$ integrin. The invention further involves treating or inhibiting pathological conditions associated therewith such as osteoporosis, humoral hypercalcemia of malignancy, Paget's disease, tumor metastasis, solid tumor growth (neoplasia), angiogenesis, including tumor angiogenesis, retinopathy including macular degeneration and diabetic retinopathy, arthritis, including rheumatoid arthritis, periodontal disease, psoriasis, smooth muscle cell migration and restenosis in a mammal in need of such treatment. Additionally, such pharmaceutical agents are useful as antiviral agents, and antimicrobials.

DETAILED DESCRIPTION

The present invention relates to a class of compounds represented by the Formula I, described above.

A halogen atom is preferably chlorine or fluorine.

The alkyl, alkoxy, alkenyl and alkynyl groups and the alkylene and alkenylene chains may be branched or straight groups or chains, respectively.

An aryl group is, e.g., an aromatic $C_6$–$C_{20}$ mono- or poly-nuclear moiety, typically phenyl, naphthyl, unsubstituted or substituted by one to three substituents independently chosen from halogen, hydroxy, $CF_3$, $C_1$–$C_4$ alkyl and $C_1$–$C_4$ alkoxy.

A $C_5$–$C_7$ monocyclic heteroaryl ring is preferably a $C_5$–$C_6$ heteromonocyclic ring, in particular selected from pyridine, pyrazine, pyridazine, pyrimidine, thiophene, pyrrole, pyrazole, imidazole, oxazole and isoxazole.

Accordingly an aralkyl group is e.g. benzyl or phenethyl, in which the phenyl ring is optionally substituted by one to three substituents independently selected from halogen, hydroxy, $CF_3$, $C_1$–$C_4$alkyl and $C_1$–$C_4$ alkoxy.

A $C_2$–$C_6$ alkenyl group is preferably an allyl group.

A $C_1$–$C_6$ alkyl group is preferably a $C_1$–$C_4$ alkyl group.

A $C_1$–$C_4$ alkyl group is preferably a methyl or ethyl group.

A $C_2$–$C_4$ alkynyl group is preferably an ethynyl group.

A $C_1$–$C_4$ alkoxy group is preferably methoxy, ethoxy, propoxy or butoxy.

Examples of pharmaceutically acceptable salts of the compounds of the invention are either those with inorganic bases, such as sodium, potassium, calcium and aluminum hydroxides, or with organic bases, such as lysine, arginine, N-methyl-glucamine, triethylamine, triethanolamine, dibenzylamine, methylbenzylamine, di-(2-ethyl-hexyl)-amine, piperidine, N-ethylpiperidine, N,N-diethylamino-ethylamine, N-ethylmorpholine, β-phenethylamine, N-benzyl-β-phenethylamine, N-benzyl-N,N-dimethylamine and the other acceptable organic amines, as well as the salts with inorganic acids, e.g. hydrochloric, hydrobromic and sulphuric acids and with organic acids, e.g. citric, tartaric, maleic, malic, fumaric, trifluoroacetic, methanesulphonic and ethanesulphonic acids.

As stated above, the present invention also includes within its scope pharmaceutically acceptable bio-precursors (otherwise known as pro-drugs) of the compounds of formula (I), i.e. compounds which have a different formula to formula (I) above, but which nevertheless upon administration to a human being are converted directly or indirectly in vivo into a compound of formula (I).

Preferred compounds of the invention are those, in formula (I), wherein R, R1, X and A are as defined above;

B is $(CH_2)_m(CH{=}CH)_pY$, wherein m=1,2,3, p=0 and Y is $CH_2$;

R2 is a phenyl, naphthyl, pyridine, pyrazine, pyridazine, pyrimidine, thiophene, pyrrole, pyrazole, imidazole, oxazole and isoxazole unsubstituted or optionally substituted as defined above; and G is selected from the group consisting of

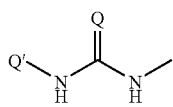

wherein Q is NH or O and Q' is H, $C_1$–$C_6$ alkyl, phenyl, or phenyl-$C_1$–$C_4$-alkyl;

a)

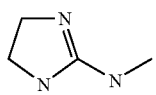

b)

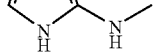

c)

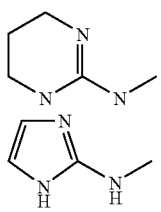

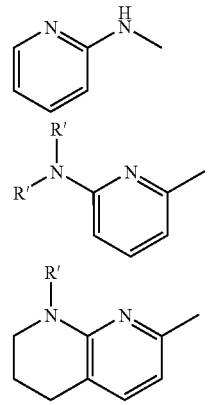

and the pharmaceutically acceptable salts, prodrugs and esters thereof.

Most preferred compounds of the invention are those wherein, in formula (I), B, X, R1, A and R are as defined above R2 is a phenyl, thiophene, oxazole, isoxazole, or a pyridine ring unsubstituted or optionally substituted as defined above; and G is selected from the group consisting of

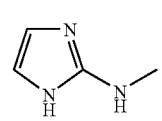 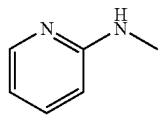

and the pharmaceutically acceptable salts, prodrugs and esters thereof.

Examples of specific preferred compounds according to the invention are the following:

3-phenyl-N-{4-[2-(2-pyridinylamino)ethyl]-3,4-dihydro-2H-1,4-benzoxazin-7-yl}-beta-alanine;

3-phenyl-N-{4-[3-(2-pyridinylamino)propyl]-3,4-dihydro-2H-1,4-benzoxazin-7-yl}-beta-alanine;

3-phenyl-N-{4-[4-(2-pyridinylamino)butyl]-3,4-dihydro-2H-1,4-benzoxazin-7-yl}-beta-alanine;

N-{4-[2-(1H-imidazol-2-ylamino)ethyl]-3,4-dihydro-2H-1,4-benzoxazin-7-yl}-3-phenyl-beta-alanine;

N-{4-[3-(1H-imidazol-2-ylamino)propyl]-3,4-dihydro-2H-1,4-benzoxazin-7-yl}-3-phenyl-beta-alanine;

N-{4-[2-(1H-imidazol-2-ylamino)butyl]-3,4-dihydro-2H-1,4-benzoxazin-7-yl}-3-phenyl-beta-alanine;

3-(3-pyridinyl)-N-{4-[2-(2-pyridinylamino)ethyl]-3,4-dihydro-2H-1,4-benzoxazin-7-yl}-beta-alanine;

3-(3-pyridinyl)-N-{4-[3-(2-pyridinylamino)propyl]-3,4-dihydro-2H-1,4-benzoxazin-7-yl}-beta-alanine;

3-(3-pyridinyl)-N-{4-[4-(2-pyridinylamino)butyl]-3,4-dihydro-2H-1,4-benzoxazin-7-yl}-beta-alanine;

N-{4-[2-(1H-imidazol-2-ylamino)ethyl]-3,4-dihydro-2H-1,4-benzoxazin-7-yl}-3-(3-pyridinyl)-beta-alanine;

N-{4-[3-(1H-imidazol-2-ylamino)propyl]-3,4-dihydro-2H-1,4-benzoxazin-7-yl}-3-(3-pyridinyl)-beta-alanine;

N-{4-[4-(1H-imidazol-2-ylamino)butyl]-3,4-dihydro-2H-1,4-benzoxazin-7-yl}-3-(3-pyridinyl)-beta-alanine;

N-{3-oxo-4-[2-(2-pyridinylamino)ethyl]-3,4-dihydro-2H-1,4-benzoxazin-7-yl}-3-phenyl-beta-alanine;

N-{3-oxo-4-[3-(2-pyridinylamino)propyl]-3,4-dihydro-2H-1,4-benzoxazin-7-yl}-3-phenyl-beta-alanine;
N-{3-oxo-4-[4-(2-pyridinylamino)butyl]-3,4-dihydro-2H-1,4-benzoxazin-7-yl}-3-phenyl-beta-alanine;
N-{4-[2-(1H-imidazol-2-ylamino)ethyl]-3-oxo-3,4-dihydro-2H-1,4-benzoxazin-7-yl}-3-phenyl-beta-alanine;
N-{4-[3-(1H-imidazol-2-ylamino)propyl]-3-oxo-3,4-dihydro-2H-1,4-benzoxazin-7-yl}-3-phenyl-beta-alanine;
N-{4-[4-(1H-imidazol-2-ylamino)butyl]-3-oxo-3,4-dihydro-2H-1,4-benzoxazin-7-yl}-3-phenyl-beta-alanine;
N-{3-oxo-4-[2-(2-pyridinylamino)ethyl]-3,4-dihydro-2H-1,4-benzoxazin-7-yl}-3-(3-pyridinyl)-beta-alanine;
N-{3-oxo-4-[3-(2-pyridinylamino)propyl]-3,4-dihydro-2H-1,4-benzoxazin-7-yl}-3-(3-pyridinyl)-beta-alanine;
N-{3-oxo-4-[4-(2-pyridinylamino)butyl]-3,4-dihydro-2H-1,4-benzoxazin-7-yl}-3-(3-pyridinyl)-beta-alanine;
N-{4-[2-(1H-imidazol-2-ylamino)ethyl]-3-oxo-3,4-dihydro-2H-1,4-benzoxazin-7-yl}-3-(3-pyridinyl)-beta-alanine;
N-{4-[3-(1H-imidazol-2-ylamino)propyl]-3-oxo-3,4-dihydro-2H-1,4-benzoxazin-7-yl}-3-(3-pyridinyl)-beta-alanine;
N-{4-[4-(1H-imidazol-2-ylamino)butyl]-3-oxo-3,4-dihydro-2H-1,4-benzoxazin-7-yl}-3-(3-pyridinyl)-beta-alanine;
3-({3-oxo-4-[3-(1H-imidazol-2-ylamino)propyl]-3,4-dihydro-2H-1,4-benzoxazin-7-yl}oxy)-3-phenylpropanoic acid;
3-({3-oxo-4-[4-(2-pyridinylamino)butyl]-3,4-dihydro-2H-1,4-benzoxazin-7-yl}oxy)-3-phenylpropanoic acid;
3-({3-oxo-4-[4-(1H-imidazol-2-ylamino)butyl]-3,4-dihydro-2H-1,4-benzoxazin-7-yl}oxy)-3-phenylpropanoic acid;
3-({3-oxo-4-[3-(2-pyridinylamino)propyl]-3,4-dihydro-2H-1,4-benzoxazin-7-yl}oxy)-3-(3-pyridinyl)propanoic acid;
3-({3-oxo-4-[4-(2-pyridinylamino)butyl]-3,4-dihydro-2H-1,4-benzoxazin-7-yl}oxy)-3-(3-pyridinyl)propanoic acid;
3-({3-oxo-4-[3-(1H-imidazol-2-ylamino)propyl]-3,4-dihydro-2H-1,4-benzoxazin-7-yl}oxy)-3-(3-pyridinyl)propanoic acid;
3-({3-oxo-4-[4-(1H-imidazol-2-ylamino)butyl]-3,4-dihydro-2H-1,4-benzoxazin-7-yl}oxy)-3-(pyridinyl)propanoic acid;
3-({3-oxo-4-[4-(2-pyridinylamino)butyl]-3,4-dihydro-2H-1,4-benzoxazin-7-yl}sulfanyl)-3-phenylpropanoic acid;
3-({3-oxo-4-[3-(1H-imidazol-2-ylamino)propyl]-3,4-dihydro-2H-1,4-benzoxazin-7-yl}sulfanyl)-3-phenylpropanoic acid;
3-({3-oxo-4-[4-(1H-imidazol-2-ylamino)butyl]-3,4-dihydro-2H-1,4-benzoxazin-7-yl}sulfanyl)-3-phenylpropanoic acid;
3-({3-oxo-4-[3-(2-pyridinylamino)propyl]-3,4-dihydro-2H-1,4-benzoxazin-7-yl}sulfanyl)-3-(3-ppyridinyl)propanoic acid;
3-({3-oxo-4-[4-(2-pyridinylamino)butyl]-3,4-dihydro-2H-1,4-benzoxazin-7-yl}sulfanyl)-3-(3-pyridinyl)propanoic acid;
3-({3-oxo-4-[3-(1H-imidazol-2-ylamino)propyl]-3,4-dihydro-2H-1,4-benzoxazin-7-yl}sulfanyl)-3-(3-pyridinyl)propanoic acid;
3-({3-oxo-4-[4-(1H-imidazol-2-ylamino)butyl]-3,4-dihydro-2H-1,4-benzoxazin-7-yl}sulfanyl)-3-(3-pyridinyl)propanoic acid;
4-{3-oxo-4-[4-(pyridin-2-ylamino)-butyl]-3,4-dihydro-2H-1,4-benzoxazin-7-yl}-3-phenylbutanoic acid;
4-{3-oxo-4-[3-(1H-imidazol-2-ylamino)-propyl]-3,4-dihydro-2H-1,4-benzoxazin-7-yl}-3-phenylbutanoic acid;
4-{3-oxo-4-[4-(1H-imidazol-2-ylamino)-butyl]-3,4-dihydro-2H-1,4-benzoxazin-7-yl}-3-phenylbutanoic acid;
4-{3-oxo-4-[4-(pyridin-2-ylamino)-butyl]-3,4-dihydro-2H-1,4-benzoxazin-7-yl}-3-(3-pyridinyl)butanoic acid;
4-{3-oxo-4-[3-(1H-imidazol-2-ylamino)-propyl]-3,4-dihydro-2H-1,4-benzoxazin-7-yl}-3-(3-pyridinyl)butanoic acid;
4-{3-oxo-4-[4-(1H-imidazol-2-ylamino)-butyl]-3,4-dihydro-2H-1,4-benzoxazin-7-yl}-3-(3-pyridinyl)butanoic acid;

A further object of the present invention is to provide a compound of formula (I) as defined above or a pharmaceutically acceptable salt, prodrug or ester thereof, for use in a method of treatment of the human or animal body by therapy, in particular for treating conditions mediated by the $\alpha_v\beta_3$ integrin.

The object of the present invention is also to provide a pharmaceutical composition comprising a pharmaceutically acceptable carrier and/or diluent and as an active principle a compound of formula (I), as herein defined, or a pharmaceutically acceptable salt thereof.

The present invention also provides the use of a compound of formula (1), as defined above, in the preparation of a medicament having $\alpha_v\beta_3$ integrin inhibiting or antagonizing activity.

The present invention also provides a method for treating conditions mediated by the $\alpha_v\beta_3$ integrin in a mammal, including humans, in need of such treatment comprising administering to said mammal an effective $\alpha_v\beta_3$ inhibiting or antagonizing amount of a compound of formula (I) as defined above or a pharmaceutically acceptable salt thereof More specifically, the present invention provides a method for inhibiting bone resorption, treating osteoporosis, inhibiting humoral hypercalcemia of malignancy, treating Paget's disease, inhibiting tumor metastasis, inhibiting neoplasia (solid tumor growth), inhibiting angiogenesis including tumor angiogenesis, treating diabetic retinopathy, inhibiting arthritis, psoriasis and periodontal disease, and inhibiting smooth muscle cell migration including restenosis.

The compounds of the invention and the salts thereof can be prepared by or in analogy to the processes described hereafter. Accordingly, compounds of formula I and the salts thereof, can be for instance obtained by a process as described here below.

A compound of formula I wherein G is as defined above and Q is different from oxygen; X, B, A, R, R1 and R2 are as defined above can be obtained by reacting a compound of formula II

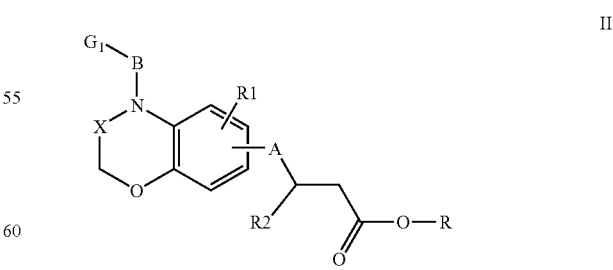

II wherein B, X, A, R, R1 and R2 are as defined above, $G_1$ is represented by G, as defined above under a) to g) wherein Q is different from oxygen and one or more nitrogens are protected with suitable protective groups, such as, for instance, carbobenzyloxy or t-butoxycarbonyl, removable with a suitable reducing agent, or with an acid, such as trifluoroacetic acid or hydrochloric or hydrobromic acid.

A compound of formula II can be obtained by:

1) reacting a compound of formula III

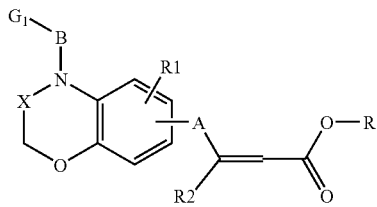

III wherein $G_1$, X, B, R, R1 and R2 are as defined above and A is NH, with a suitable reducing agent, such as an alkali metal borohydride or an alkali metal cyanoborohydride thus obtaining a compound of formula II wherein $G_1$, X, B, R, R1 and R2 are as defined above and A is NH. A compound of formula III, wherein $G_1$, B, X, R, R1 and R2 are as defined above and A is NH, can, in turn, be obtained by reacting a compound of formula IV

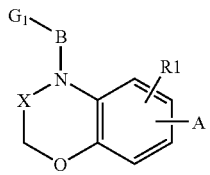

IV wherein $G_1$, B, X, and R1 are as defined above and A is $NH_2$, with a compound of formula V

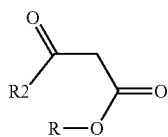

V wherein R and R2 are as defined above; or

2) Reacting a compound of formula IV wherein $G_1$, B, X, and R1 are as defined above and A is SH, with a compound of formula VI

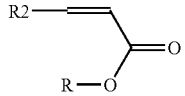

VI wherein R and R2 are as defined above, thus obtaining a compound of formula II wherein G, X, B, R, R1 and R2 are as defined above, and A is S; or 3) Reacting compound of formula IV where $G_1$, B, X and R1 are as defined above and A is OH with a compound of formula VII

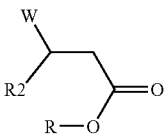

VII wherein R and R2 are as defined above, and W is Cl, Br, I, OH or $OSO_2C_1$–$C_4$-alkyl or $OSO_2$Aryl, thus obtaining a compound of formula II wherein G, X, B, R, R1 and R2 are as defined above, and A is O; or 4) Reacting a compound of formula II, wherein $G_1$, X, B, R, R1 and R2 are as defined above, and A is S, with an oxydizing agent such as $NaIO_4$, oxone, $H_2O_2$ or a peracid, thus obtaining a compound of formula II wherein $G_1$, X, B, R1, R2 and R are as defined above and A is $S(O)_n$ wherein n is 1 or 2, i.e. A is a sulfoxide or sulfone group; or 5) Reacting a compound of formula VIII

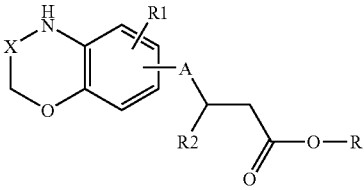

VIII wherein X, R, R1, R2 are as defined above, and A is $CH_2$, with a compound of formula IX $G_1$-B-W  IX wherein $G_1$, B and W are as defined above, thus obtaining a compound of formula II wherein $G_1$, X, B, R1, R2 and R are as defined above and A is $CH_2$. A compound of formula VIII, as defined above, can, in turn, be obtained by reacting a compound of formula X

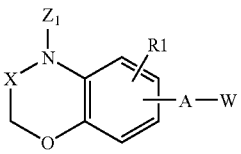

X wherein X and R1 are as defined above, A is $CH_2$, W is selected from Cl or Br and $Z_1$ is a suitable amide protecting group, such as a p-methoxybenxyl group, with magnesium followed by addition of the resulting compound to a compound of formula VI, wherein R and R2 are as described above, in the presence of suitable metal salts, like copper salts, followed by removal of $Z_1$.

A compound of formula IV, as defined above wherein A is NH$_2$, can be obtained by reduction of a compound of formula XI

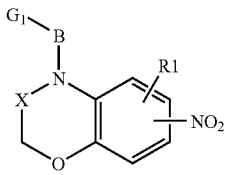

XI wherein G$_1$, X, B and R1 are as defined above.

A compound of formula IV, wherein G$_1$, X, B and R1 are as defined above and A is SH or OH can be obtained by a compound of formula XII

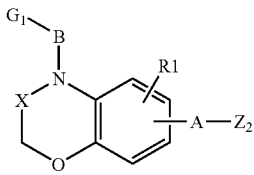

XII wherein, X, B and R1 are as defined above, A is S or O and Z$_2$ is a suitable protecting group for a —OH or a —SH moiety, such as methyl, p-methoxybenzyl, t-butyldimethylsilyl, p-nitrobenzyl, by removal of the Z$_2$ protecting group.

A compound of formula XI can be obtained by reacting a compound of formula XIII

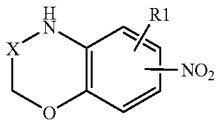

XIII wherein X and R1 are as defined above, with a compound of formula IX, as defined above.

A compound of formula XII can be obtained by reacting a compound of formula XIV

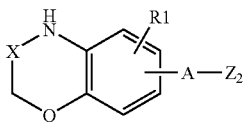

XIV wherein A, X, R1, and Z$_2$ are as defined above, with a compound of formula IX, as defined above.

A compound of formula I, wherein B, X, R, R1, R2 are as defined above, A is CH$_2$, O or S, and G is as defined under a) wherein Q is oxygen, can be obtained by reacting a compound of formula XV

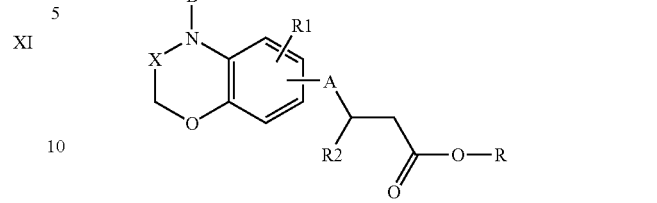

XV wherein B, X, R, R1, R2 are as defined above and A is CH$_2$, O or S, with an inorganic cyanate, such as sodium or potassium or ammonium cyanate, or with an isocyanate of formula Q'NCO, wherein Q' is as described above.

A compound of formula I, wherein B, X, R, R1, R2 are as defined above, A is CH$_2$, O or S, and G is as defined under a) wherein Q is different from oxygen, or under b) and c), and Q' is hydrogen, can be obtained by reacting a compound of formula XV with a suitable guanylating agent, such as, for instance, N,N'-di-t-butoxycarbonyl-N''-triflylguanidine or 2-methylthio-2-imidazoline hydriodide or 2-methylthio-1,4,5,6-tetrahydropyrimidine hydriodide, followed by removal of the protecting groups in the case where the guanilating agent is N,N'-di-t-butoxycarbonyl-N''-triflylguanidine.

A compound of formula XV, as defined above, can be obtained by reaction of a compound of formula VIII, wherein X, R, R1, R2 are as defined above, and A is CH$_2$, O or S, with a compound of formula XVI

XVI wherein B and W are as defined above and Z$_3$ is a suitable amino protecting group such as, for instance, carbobenzyloxy or t-butoxycarbonyl, followed by removal of Z$_3$.

A compound of formula I, wherein B, X, R, R1, R2 are as defined above, A is NH, and G is as defined under a) wherein Q is oxygen, can be obtained by reacting a compound of formula XVII

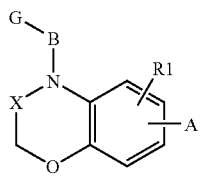

XVII wherein B and R1 are as defined above, G is as defined under a) wherein Q is oxygen, and A is NH$_2$, with a compound of formula V, followed by reduction of the product with an alkali metal borohydride or an alkali metal cyanoborohydride. A compound of formula XVII, as defined above, can be obtained in analogy to the procedures described for the synthesis of compounds of formula IV, provided that G, as defined above, is substituted for G$_1$.

A compound of formula I, wherein B, X, R, R1, R2 are as defined above, A is NH, and G is as defined under a) wherein Q is different from oxygen, or under b) or c), and Q' is hydrogen, can be obtained by reacting a compound of formula XV, wherein B, X, R, R1 and R2 are as defined above, and A is NH, with a suitable guanilating agent, such as, for instance, N,N'-di-t-butoxycarbonyl-N''-triflylguanidine or 2-methylthio-2-imidazoline hydriodide or 2-methylthio-1,4,5,6-tetrahydropyrimidine hydriodide, followed by removal of the protecting groups in the case where the guanilating agent is N,N'-di-t-butoxycarbonyl-N''-triflylguanidine.

A compound of formula XV, wherein B, X, R, R1 and R2 are as defined above, and A is NH, in turn, can be obtained by reacting a compound of formula XIII, as defined above, with a compound of formula XVI, as defined above, followed by: a) reduction of the nitro group, b) reaction with a compound of formula V, as defined above, c) reduction of the resulting compound with an alkali metal borohydride or an alkali metal cyanoborohydride, d) removal of the protecting group $Z_3$.

A compound of formula X or XIII or XIV, as defined above, can be prepared according to general methods described in the literature.

Additionally, a compound of formula I can be obtained by a process which comprises:
a) converting a compound of formula (I) into another compound of formula (I), or separating a single isomer of a compound of formula (I) from a mixture thereof, or converting a compound of formula (I) into a salt thereof, or converting a salt of a compound of formula (I) into a free compound of formula (I);
b) reacting a compound of formula I wherein G, X, B, A R1 and R2 are as defined above and R is different from hydrogen with aqueous acids or aqueous bases thus obtaining a compound of formula I wherein R is hydrogen;

The compounds described above can be prepared as exemplified in the following procedures.

In a typical procedure, a compound of formula I, as defined above, can be obtained by treatment of a compound of formula II, as defined above, with hydrogen in the presence of a suitable catalyst, such as palladium on carbon, in a solvent like a lower alcohol or dioxane, or by treatment with trifluoroacetic acid or hydrobromic acid in acetic acid, followed by isolation of the product by chromatography.

In a typical procedure for the preparation of a compound of formula III, as defined above, a compound of formula IV, as defined above, a keto-ester of formula V and anhydrous calcium sulfate and catalytic acetic acid are mixed in an anhydrous alcohol, such as ethanol, and refluxed for 24 to 96 hours. The compound is isolated by column chromatography. The reduction of a compound of formula III with sodium cyanoborohydride in ethanol provides a compound of formula II, as defined above and wherein A is NH.

In a typical procedure for the preparation of a compound of formula II, as defined above and wherein A is S, a compound of formula IV, as defined above and wherein A is SH, is added to a solution of a compound of formula VI, as defined above, in a solvent like tetrahydrofuran or dichloromethane, in the presence of a small amount of an organic base such as diazabicycloundecene (DBU). The reaction is allowed to proceed from 12 to 48 hours, at a temperature from about 20 to about 40° C., and the product isolated by column chromatography.

In a typical procedure for the preparation of a compound of formula II, as defined above and wherein A is O, to a dichloromethane or tetrahydrofuran solution containing a compound of formula IV, as defined above and wherein A is OH, triphenylphosphine and a compound of formula VII, as defined above and wherein W is OH, a solution of an alkyl azodicarboxylate in dichloromethane or tetrahydrofuran is added and the mixture stirred at a temperature from room temperature to about 40° C. for 1 to 6 hours. The product is then isolated by column chromatography. The procedure described above is similar to procedures disclosed in the literature (see, for instance, KRCHNAK, V., FLEGELOVA, Z., WEICHSEL, A. S., LEBL, M. *Tetrahedron Letters* 1995, 36, 6193–6196; or BROWN, R. F. C., JACKSON, W. R., McCARTHY, T. D. *Tetrahedron* 1994, 18, 5469–5488).

In a typical procedure for the preparation of a compound of formula II, as defined above and wherein A is $SO_2$, a compound of formula II, as defined above and wherein A is S, is treated with 30% aqueous $H_2O_2$ in an alcohol as a solvent, or with $NaIO_4$ in water and methanol, or acetone and water, (as described, for instance, in BEIER, C., SCHAUMANN, E. *Synthesis* 1997, 11, 1296–1300).

In a typical procedure for the preparation of a compound of formula II, as defined above and wherein A is SO, a compound of formula II, as defined above and wherein A is S, is treated with oxone in a mixture methanol/water as a solvent (as described, for instance, in HINTERBERGER, S., HOFER, O., GREGER, H. *Tetrahedron* 1998, 54, 487–496).

In a typical procedure for the preparation of a compound of formula II, as defined above and wherein A is $CH_2$, a Grignard reagent obtained from a compound of formula X, as defined above and wherein W is Cl or Br and P1 is p-methoxybenzyl, is added to a mixture of cuprous iodide (CuI) and dry tetramethylene diamine (TMEDA) in dry tetrahydrofuran at a temperature of about −78° C. The mixture is then stirred at about −78° C. for between 15 minutes to 1 hours, then a tetrahydrofuran solution of chlorotrimethyl silane and a compound of formula IV, as defined above, is added and the temperature allowed to rise to about −30° C. After a period of 12 to 36 hours, the reaction is treated with a saturated aqueous solution of ammonium chloride and ammonium hydroxide and extracted with a suitable solvent, such as dichloromethane, chloroform, diethylether, ethyl acetate and the product isolated by column chromatography (see, for instance, VAN HEERDEN, P. S., BEZUIDENHOUDT, B. C. B., FERREIRA, D. *Tetrahedron* 1996, 52, 12313–12322; or VAN HEERDEN, P. S., BEZUIDENHOUDT, B. C. B., FERREIRA, D. *J. Chem. Soc. Perk. Trans.* 1, 1997, 1141–1146). Then, the p-methoxybenzyl group is removed by catalytic hydrogenolysis, using a supported metal catalyst, such as palladium on carbon in a solvent like methanol or ethanol, to give a compound of formula VIII, as defined above and wherein A is $CH_2$. A compound of formula VIII, as defined above, is then reacted with a compound of formula IX, as defined above and wherein W is typically $OSO_2CH_3$, in the presence of an organic base, such as potassium hexamethyldisilazide in a solvent like tetrahydrofuran or dimethylformamide or mixtures thereof, at a temperature from room temperature to about 100° C. for 1 to 6 hours, the product isolated by column chromatography thus giving a compound of formula II, as defined above and wherein A is $CH_2$.

In typical procedure for the preparation of a compound of formula IV, as defined above and wherein A is $NH_2$, a compound of formula XI, as defined above, is reduced by treatment with a mixture of titanium tetrachloride and tin dichloride in a solvent like tetrahydrofuran or diisopropyl ether or diethyl ether, at a temperature from about 20 to about 40° C. and under an atmosphere of an inert gas. A compound of formula XI, as defined above, can be obtained by treatment of a compound of formula XIII, as defined above, with a compound of formula IX, as defined above and wherein W is typically $OSO_2CH_3$, in the presence of an organic base, such as potassium hexamethyldisilazide in a solvent like tetrahydrofuran or dimethylformamide or mixtures thereof, at a temperature from room temperature to about 100° C. for 1 to 6 hours, and the product isolated by column chromatography.

In typical procedure for the preparation of a compound of formula XII, as defined above and wherein A is O or S and $Z_2$ is a protecting group such as methyl, ethoxymethyl, p-methoxybenzyl, t-butyldimethylsilyl, t-butyldiphenylsilyl, p-nitrobenzyl or other suitable protecting group (see: GREENE, T. W., WUTS, P. G. M. Protective group in organic synthesis, Wiley, 1999), a compound of formula XIV, as defined above, is reacted with a compound of formula IX, as defined above and wherein W is typically $OSO_2CH_3$, in the presence of an organic base, such as potassium hexamethyldisilazide in a solvent like tetrahydrofuran or dimethylformamide or mixtures thereof, at a temperature from room temperature to about 100° C. for 1 to 6 hours.

In typical procedure for the preparation of a compound of formula I, wherein B, X, R, R1, R2 are as defined above, A is $CH_2$, O or S, and G is as defined under a) wherein Q is oxygen and Q' is hydrogen, a compound of formula XV, as defined above, is reacted with a cyanate salt, as e.g. an ammonium or sodium or potassium salt, in solvent such as acetic acid or water, at a temperature from about 50 to about 100° C., for 2 to 12 hours (see, as an example, Organic Synthesis vol. IV, p. 49, 1963).

In typical procedure for the preparation of a compound of formula I, wherein B, X, R, R1, R2 are as defined above, A is $CH_2$, O or S, and G is as defined under a) wherein Q is oxygen and Q' is different from hydrogen, a compound of formula XV, as defined above, is reacted with an isocyanate of formula Q'NCO, wherein Q' is as defined above, in a solvent like dichloromethane, acetonitrile, tetrahydrofuran, dioxane or toluene, in the presence of triethylamine, at a temperature from room temperature to about 100° C. and for 4 to 24 hours. The resulting compound is isolated by column chromatography.

In a typical procedure for the preparation of a compound of formula I, wherein B, X, R, R1, R2 are as defined above, A is $CH_2$, O or S, and G is as defined under a) wherein Q is different from oxygen, or under b) and c), and Q' is hydrogen, a compound of formula XV is treated with a suitable guanylating agent, like N,N'-di-t-butoxycarbonyl-N"-triflylguanidine or 2-methylthio-2-imidazoline hydriodide or 2-methylthio-1,4,5,6-tetrahydropyrimidine hydriodid in a solvent like dichloromethane, tetrahydrofuran, dioxane or a lower alcohol, at a temperature from room temperature to reflux, for 24 to 72 hours, followed by evaporation of the solvent and isolation of the product by chromatography. In typical procedure for the preparation of a compound of formula XV, as defined above, a compound of formula VIII, wherein X, R1, R2 are as defined above, R is different from hydrogen and A is $CH_2$, O or S, with a compound of formula XVI, as defined above and wherein W is Br or $OSO_2CH_3$, in the presence of an organic base, such as potassium hexamethyldisilazide in a solvent like tetrahydrofuran or dimethylformamide or mixtures thereof, at a temperature from room temperature to 100° C. for 1 to 6 hours. The resulting compound is isolated by column chromatography, and the protecting group $Z_3$ is then removed following the standard procedures described in the literature (see: GREENE, T. W., WUTS, P. G. M. Protective group in organic synthesis, Wiley, 1999).

In typical procedure for the preparation of a compound of formula I, wherein B, X, R, R1, R2 are as defined above, A is NH, G is as defined under a) wherein Q is oxygen and Q' is as defined above, a compound of formula XVII, as defined above, is mixed with a keto-ester of formula V in the presence of anhydrous calcium sulfate and catalytic acetic acid, in a solvent like an anhydrous alcohol, such as ethanol, and refluxed for 24 to 96 hours. The compound is isolated by column chromatography, then is treated with sodium cyanoborohydride in ethanol thus giving a compound of formula I, as defined above. A compound of formula XVII, as defined above, can be obtained using the same procedure described above for the synthesis of compounds of formula IV, provided that G, as defined under a), is substituted for $G_1$, and wherein A is $NH_2$.

In typical procedure for the preparation of a compound of formula I, wherein B, X, R, R1, R2 are as defined above, A is NH, G is as defined under a) wherein Q is different from oxygen, or under b) or c), and Q' is hydrogen, a compound of formula XV, wherein B, X, R, R1 and R2 are as defined above, and A is NH is reacted with a suitable guanylating agent, like N,N'-di-t-butoxycarbonyl-N"-triflylguanidine or 2-methylthio-2-imidazoline hydriodide or 2-methylthio-1,4,5,6-tetrahydropyrimidine hydriodid in a solvent like dichloromethane, tetrahydrofuran, dioxane or a lower alcohol, at a temperature from room temperature to reflux, for 24 to 72 hours, followed by evaporation of the solvent and isolation of the product by chromatography. In the case where the guanilating agent is N,N'-di-t-butoxycarbonyl-N"-triflylguanidine, the product is then treated with trifluoroacetic acid, to remove the nitrogen protecting groups, the trifluoroacetic acid is evaporated to afford the desired compound. A compound of formula XV, as defined above, can be obtained using the synthetic sequence described before and applying some of the experimental procedures described before.

In a typical procedure, a compound of formula I, as defined above and wherein R is hydrogen, is obtained by treatment of a compound of formula I, as defined above and wherein R is different form hydrogen, with a mixture of an aqueous acid, like hydrochloric acid, and a lower alcohol or dioxane, at a temperature from room temperature to about 40° C., for 1 to 24 hours.

Alternatively, a compound of formula I, as defined above and wherein R is different form hydrogen, is treated with an aqueous base, like sodium or lithium or potassium hydroxide, in a solvent like methanol or ethanol or dioxane, at a temperature from room temperature to about 40° C., for 1 to 24 hours. The solution is then treated with an acid and the compound filtered.

A compound of formula X or XIII or XIV, as defined above, can be obtained according to general synthetic methods for 1,4-benzoxazines as described, for instance, in METHODS OF ORGANIC CHEMISTRY (HOUBEN-WEIL), volume E 9a, pp. 141–177, George Thieme Verlag, Stuttgart 1997, or by suitable modifications of such methods as known to those skilled in the art. Also the optional salification of a compound of formula (I) as well as the conversion of a salt into the free compound and the separation of a mixture of isomers into the single isomers may be carried our by conventional methods. For example, the separation of optical isomers may be carried out by salification with an optically active base or acid and by subsequent fractional crystallisation of the diastereoisomeric salts, followed by recovering of the optically active isomeric acids or bases, respectively.

When in the compound of formula (I), and in the intermediate products thereof, groups are present which need to be protected before submitting them to the here-above illustrated reactions, they may be protected before the reactions take place and then deprotected, according to methods well known to those skilled in the art.

The compounds of formula (I) and the pharmaceutically acceptable salts thereof are herein defined as the "compounds of the present invention", the "compounds of the invention" and/or the "active principles of the pharmaceutical compositions of the invention".

The following examples describe the invention without limiting it.

EXAMPLE 1

The compounds of the Example 1 can be equally named as 3-amino-3-phenylpropanoic acid derivatives or 3-phenyl-beta-alanine derivatives. The preparation of compounds 3-{4-[3-(N-(2-pyridinyl)amino)propyl]-3-oxo-3,4-dihydro-2H-1,4-benzoxazin-7-yl)amino}-3-phenylpropanoic acid, 3-{4-[4-(N-(2-pyridinyl)amino)butyl]-3-oxo-3,4-dihydro-2H-1,4-benzoxazin-7-yl)amino}-3-phenylpropanoic acid, and 3-{4-[3-(N-(2-pyridinyl)amino)propyl]-3,4-dihydro-2H-1,4-benzoxazin-7-yl)amino}-3-phenylpropanoic acid are provided. The aforementioned compounds can be synthesized as reported in Scheme 1.

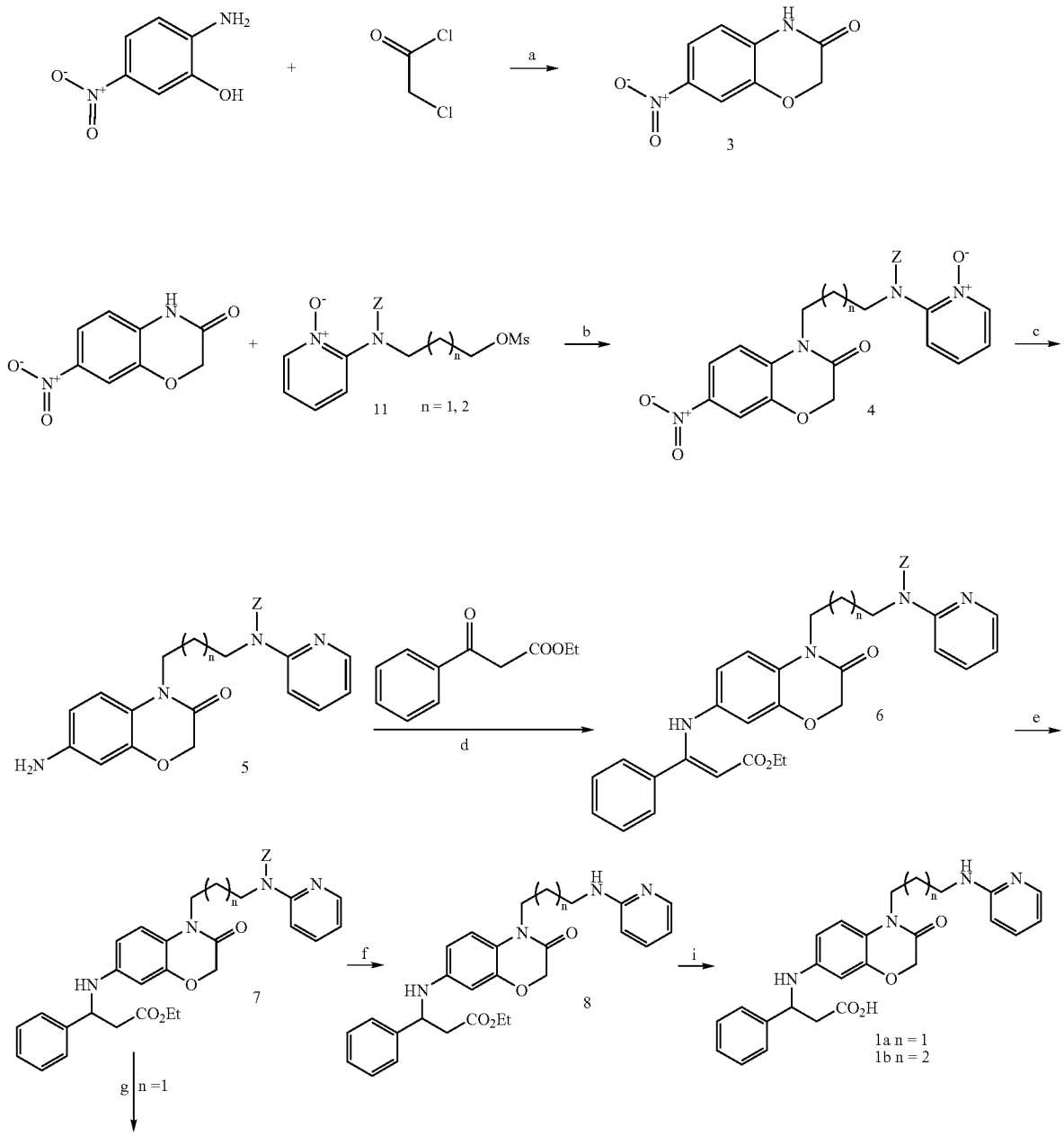

Scheme 1.

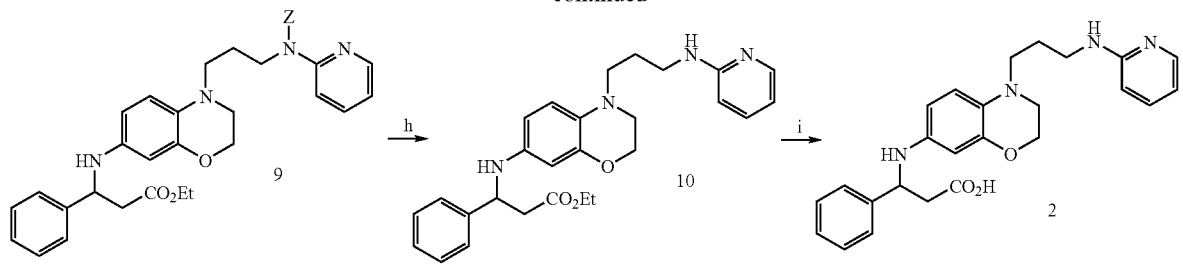

a) TEA, DMAP, CH₂Cl₂, reflux; b) KHMDS, THF/DMF, 80° C., 3 + 5 h; c) 2 eq. TiCl₄/SnCl₂; d) CaSO₄, EtOH (58%); e) NaCNBH₃ (88%); f) HBr/CH₃COOH, r.t. overnight; g) BH₃, THF; h) HBr/CH₃COOH, 70° C., 1 h; i) NaOH, EtOH or dioxane, r.t.;

The alkylating agents 3-{[N-benzyloxycarbonyl-N-(1-oxido-2-pyridinyl)amino]}-alkyl methanesulfonates have been prepared as described in Scheme 2.

Scheme 2

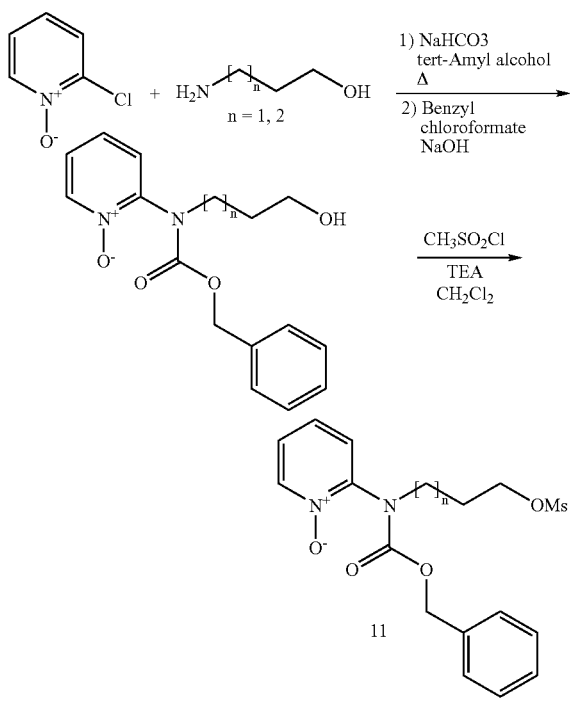

3-{4-[3-(N-(2-pyridinyl)amino)propyl]-3-oxo-3,4-dihydro-2H-1,4-benzoxazin-7-yl)amino}-3-phenylpropanoic acid (or N-{3-oxo-4-[3-(2-pyridinylamino)-propyl]-3,4-dihydro-2H-1,4-benzoxazin-7-yl}-3-phenyl-beta-alanine) (1a)

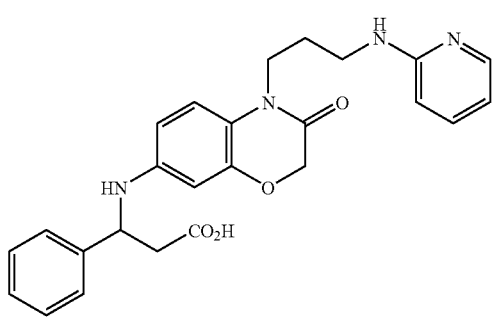

7-nitro-3-oxo-3,4-dihydro-2H-1,4-benzoxazine, 3

To a stirred solution of 2-amino-5-nitrophenol (10 g, 0.065 mol), triethylamine (13.79 g, 0.136 mol) and dimethylaminopyridine (0.16 g, 0.0013 mol) in anhydrous dichloromethane (200 mL), at 0° C. and under nitrogen atmosphere, chloroacetylchloride (7.69 g, 0.068 mol) was added. The mixture was refluxed for 10 h, poured into aqueous sodium bisulfate, extracted with dichloromethane and the residue purified by flash chromatography (petroleum ether/ethyl acetate 1:1, then pure ethyl acetate). The fraction containing the compound were evaporated, the residue treated with diethylether and filtered to give 9.9 g (79%) of the title compound as a yellow solid.

3-{[N-benzyloxycarbonyl-N-(1-oxido-2-pyridinyl)amino]}propyl methanesulfonate, 11 (n=1)

3-[N-benzyloxycarbonyl-N-(1-oxido-2-pyridinyl)amino] propanol was prepared by reaction of 3-[N-(1-oxido-2-pyridinyl)amino] propanol (obtained as described in MILLER, W. H. et al. Bioorg. Med. Chem. Lett. 1999, 9 1807–1812) with benzyl chloroformate according to the standard procedure.

To a stirred solution of 3-[N-benzyloxycarbonyl-N-(1-oxido-2-pyridinyl)-amino] propanol (3 g, 9.92 mmol) and triethylamine (1.2 g, 11.91 mmol) in anhydrous dichloromethane, kept at 0° C. under nitrogen atmosphere, methanesulfonyl chloride (1.36 g, 11.91 mmol) was added, the reaction was allowed to warm to room temperature and stirred for 1 h. The mixture was washed with ice-water, dried with sodium sulfate, filtered and concentrated to give 2.17 g (61%) of 3-[N-benzyloxycarbonyl-N-(1-oxido-2-pyridinyl)amino]-propyl methanesulfonate which, when required, was purified by flash chromatography (dichloromethane/methanol 95:5).

7-nitro-4-{3-[N-benzyloxycarbonyl-N-(1-oxido-2-pyridinyl)amino]propyl}-3-oxo-3,4-dihydro-2H-1,4-benzoxazine, 4 (n=1)

To a stirred solution of 3 (1 g, 5.15 mmol) in THF/DMF 3:1 (15 mL) cooled to 0° C. under nitrogen atmosphere, potassium hexamethyldisilazide (1.33 g, 6.69 mmol) was added and the mixture stirred for 10 minutes. Then, 3-[N-benzyloxycarbonyl-N-(1-oxido-2-pyridinyl)amino]propyl methanesulfonate (2.0 g, 5.26 mmol) in THF was added in one portion, the reaction mixture heated at 80° C. for 3 hours, allowed to cool to room temperature and left standing overnight under a vigorous stirring. The solvent was removed, the residue taken up with water, extracted with dichloromethane, the organic fractions washed with aqueous sodium bisulfate followed by sodium bicarbonate solution. After drying over sodium sulfate, the solvent was evaporated, the residue was purified by flash chromatography (dichloromethane/methanol 95:5) to give 0.83 g (34%) of the desired compound.

7-amino-4-{3-[N-benzyloxycarbonyl-N-(2-pyridinyl) amino]propyl}-3-oxo-3,4-dihydro-2H-1,4-benzoxazine, 5 (n=1)

In a round flask containing tetrahydrofuran under nitrogen atmosphere, were added titanium (IV) chloride (5 mL, 5.02 mmol) followed by stannous chloride dihydrate (1.2 g, 5.02 mmol). The mixture was stirred 1 h at room temperature, then compound 4 (1 g, 2.1 mmol) was added. The mixture was heated 3 h to 40° C., stannous chloride dihydrate (1.2 g, 5.02 mmol) and ethanol (6 mL) were added and the mixture heated for further 3 h at 40° C. The solvent was evaporated, ice and aqueous sodium bicarbonate added, and the mixture extracted with ethyl acetate. The organic layers were combined, dried over sodium sulphate, the solvent evaporated and the residue purified by flash chromatography eluting with petroleum ether/ethyl acetate 1:1, yielding 0.63 g (70%) of the title compound as an oil.

$^1$H-NMR (400 MHz), δ (DMSO-$d_6$): 1.80 (m, 2H, $CH_2$), 3.78 (t, 2H, J=7.3, $CH_2$NCbz), 3.91 (t, 2H, J=7.3, —$CH_2$NCO), 4.42 (s, 2H, —$CH_2$O—), 4.97 (s, 2H, $NH_2$), 5.14 (s, 2H, $CH_2$Ph), 6.20 (m, 2H, ArH), 6.73 (d, 1H, J=9, ArH), 7.17 (m, 1H, H-5 pyridine), 7.32 (m, 5H, PhH), 7.58 (m, 1H, H-3 pyridine), 7.77 (m, 1H, H-4 pyridine), 8.38 (m, 1H, H-6 pyridine).

Ethyl 3-{4-[3-(N-benzyloxycarbonyl-N-(2-pyridinyl) amino)propyl]-3-oxo-3,4-dihydro-2H-1,4-benzoxazin-7-yl) amino}-3-phenylpropenoate, 6 (n=1)

A mixture of 5 (n=1, 0.85 g, 1.96 m-mol), ethyl benzoyl acetate (0.45 g, 2.36 mmol), anhydrous calcium sulfate (0.67 g, 4.91 mmol) and acetic acid (0.1 mL) in ethanol (20 mL) was refluxed for 80 h. The inorganic salts were filtered, the solvent evaporated and the residue purified by flash chromatography, eluting with petroleum ether/ethyl acetate 1:1, to give 0.7 g (59%) of 6 (n=1).

$^1$H-NMR (400 MHz), δ (DMSO-$d_6$): 1.22 (t, 3H, J=7.1, $CH_3$CH$_2$OCO), 1.80 (m, 2H, CH$_2$$CH_2$CH$_2$), 3.78 (t, 2H, J=7.3, CH$_2$NCbz), 3.88 (t, 2H, J=7.3, —CH$_2$NCO), 4.12 (q, 2H, J=7.1, CH$_3$$CH_2$OCO), 4.46 (s, 2H, —CH$_2$O—), 4.90 (s, 1H, CH=$CH$COO), 5.11 (s, 2H, CH$_2$Ph), 6.28 (dd, 1H, J=2.6, 8.8, ArH), 6.36 (d, 1H, J=2.6, ArH), 6.79 (d, 1H, J=8.8, ArH), 7.18 (m, 1H, H-5 pyridine), 7.30 (m, 10H, PhH), 7.57 (m, 1H, H-3 pyridine), 7.76 (m, 1H, H-4 pyridine), 8.32 (m, 1H, H-6 pyridine), 10.06 (s, 1H, NH).

Ethyl 3-{4-[3-(N-benzyloxycarbonyl-N-(2-pyridinyl) amino)propyl]-3-oxo-3,4-dihydro-2H-1,4-benzoxazin-7-yl) amino}-3-phenylpropanoate, 7 (n=1)

To a stirred solution of 6 (0.85 g, 1.4 mmol) and acetic acid (5 mL) in ethanol (50 mL) under nitrogen atmosphere at 0° C., sodium cyanoborohydride (0.44 g, 7.0 mmol) was added in one portion and the reaction allowed to warm to room temperature and stirred for 3 h. After removal of the solvent, the residue was dissolved in dichloromethane and the organic phase washed with saturated sodium bicarbonate, dried, filtered and evaporated to give 0.74 g (88%) of 7 (n=1).

$^1$H-NMR (400 MHz), δ (DMSO-$d_6$): 1.10 (t, 3H, J=7.1, $CH_3$CH$_2$OCO), 1.78 (m, 2H, CH$_2$$CH_2$CH$_2$), 2.72 (m, 2H, $CH_2$COOEt), 3.75 (t, 2H, J=7.1, CH$_2$NCbz), 3.89 (t, 2H, J=7.1, —CH$_2$NCO), 4.00 (q, 2H, J=7.1, CH$_3$$CH_2$OCO), 4.39 (s, 2H, —CH$_2$O—), 4.71 (m, 1H, Ph$CH$NH), 5.10 (s, 2H, OCH$_2$Ph), 6.20 (m, 3H, ArH+NH), 6.71 (d, 1H, J=9.5, ArH), 7.10–7.40 (m, 11H, PhH+H-5 pyridine), 7.57 (m, 1H, H-3 pyridine), 7.75 (m, 1H, H-4 pyridine), 8.32 (m, 1H, H-6 pyridine).

Ethyl 3-{4-[3-(N-(2-pyridinyl)amino)propyl]-3-oxo-3,4-dihydro-2H-1,4-benzoxazin-7-yl)amino}-3-phenylpropanoate, 8 (n=1)

Compound 7 (0.75 g, 1.2 mmol) in acetic acid was cooled to 5–7° C., 30% hydrobromic acid in acetic acid (10 mL) was added and the mixture stirred at room temperature overnight. The solvent was removed, the residue cooled and treated with saturated sodium bicarbonate at 5° C. The aqueous mixture was extracted with dichloromethane. The organic extracts were dried over sodium sulfate, evaporated to small volume and the residue purified by flash chromatography (dichloromethane/methanol 95:5) to give 0.3 g (50%) of 8 (m=1).

$^1$H-NMR (400 MHz), δ (DMSO-$d_6$): 1.10 (t, 3H, J=7.1, $CH_3$CH$_2$OCO), 1.73 (m, 2H, CH$_2$$CH_2$CH$_2$), 2.73 (m, 2H, $CH_2$COOEt), 3.21 (m, 2H, $CH_2$NHPyr), 3.81 (dd, 2H, J=7.1, 7.1, CH$_2$NCO), 4.01 (q, 2H, J=7.1, CH$_3$$CH_2$OCO), 4.44 (s, 2H, —CH$_2$O—), 4.71 (m, 1H, Ph$CH$NH), 6.23 (m, 2H, 2ArH), 6.41 (m, 3H, NH+H-5 pyridine+H-3 pyridine), 6.81 (d, 1H, J=8.5, ArH), 7.20–7.40 (m, 5H, PhH), 7.90 (m, 1H, H-6 pyridine).

3-{4-[3-(N-(2-pyridinyl)amino)propyl]-3-oxo-3,4-dihydro-2H-1,4-benzoxazin-7-yl)amino}-3-phenylpropanoic acid, 1a To a stirred solution of 8 (m=1, 0.25 g, 0.53 mmol) in dioxane (12 mL) at 5° C., 2N sodium hydroxide (5 ml) was added and the mixture stirred overnight. The pH was adjusted to neutrality by adding the stoichiometric amount of 2N hydrochloric acid. Silica gel was added to the mixture, the solvent was evaporated and the residue purified by flash chromatography (dichloromethane/methanol/acetic acid 85:15:1) to give 0.17 g (76%) of compound 1a as a white solid.

MS: m/z 447 (M+H$^+$).

$^1$H-NMR (400 MHz), δ (DMSO-$d_6$): 1.71 (m, 2H, CH$_2$$CH_2$CH$_2$), 2.60 (m, 2H, $CH_2$COOH), 3.20 (m, 2H, $CH_2$NHPyr), 3.80 (m, 2H, CH$_2$NCO), 4.43 (s, 2H, —CH$_2$O—), 4.67 (m, 1H, Ph$CH$NH), 6.19 (m, 2H, ArH), 6.25(broad s, 1H, NH), 6.40 (m, 3H, NH+H-5 pyridine+H-3 pyridine), 6.80 (d, 1H, J=8.5, ArH), 7.18–7.40 (m, 6H, PhH+H-4 pyridine), 7.89 (m, 1H, H-6 pyridine).

3-{4-[4-(N-(2-pyridinyl)amino)butyl]-3-oxo-3,4-dihydro-2H-1,4-benzoxazin-7-yl)amino}-3-phenylpropanoic acid (or 3-phenyl-N-{4-[3-(2-pyridinyl-amino)butyl]-3,4-dihydro-2H-1,4-benzoxazin-7-yl}-beta-alanine), 1b

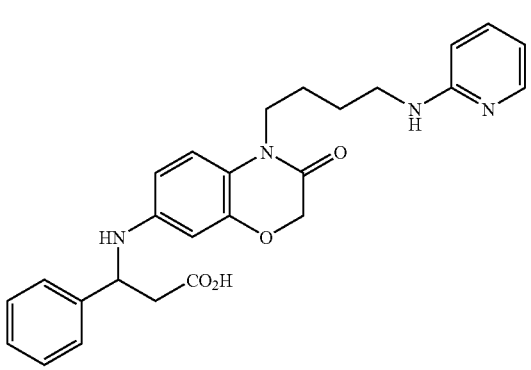

1b

Compound 1b has been synthesized as reported in Scheme 1 and following the procedure described above for compound 1a. The alkylating agent 4-[N-benzyloxycarbonyl-N-(1-oxido-2-pyridinyl)amino] butyl methansulfonate 11 (n=2) has been prepared from the corresponding alcohol as described above. Intermediates 4 to 8 (n=2) and the final compound have been obtained with yields comparable to those of the lower homologue.

$^1$H-NMR (400 MHz), δ (DMSO-$d_6$): 1.50 (m, 4H, $CH_2$ $\underline{CH_2CH_2}CH_2$), 2.60 (m, 2H, $\underline{CH_2}COOH$), 3.19 (m, 2H, $\underline{CH_2}NHPyr$), 3.75 (m, 2H, $CH_2NCO$), 4.42 (s, 2H, $CH_2O$), 4.68 (m, 1H, Ph$\underline{CH}NH$), 6.16 (d, 1H, J=2.5, ArH), 6.20 (dd, 1H, J=2.5, 8.7, ArH), 6.30 (broad s, 1H, NH), 6.40 (m, 3H, NH+H-5 pyridine+H-3 pyridine), 6.80 (d, 1H, J=8.7, ArH), 7.19 (m, 1H, H-4 pyridine), 7.27–7.40 (m, 5H, PhH), 7.89 (m, 1H, H-6 pyridine).

3-{4-[3-(N-(2-pyridinyl)amino)propyl]-3,4-dihydro-2H-1,4-benzoxazin-7-yl)amino}-3-phenylpropanoic acid (or N-{4-[3-(2-pyridinylamino)propyl]-3,4-dihydro-2H-1,4-benzoxazin-7-yl}-3-phenyl-beta-alanine), 2,

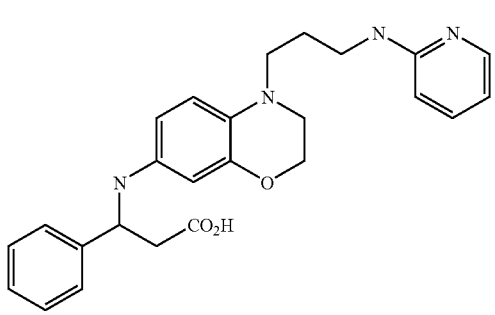

2

Compound 2 has been synthesized from 7 (n=1) as reported in Scheme 1.

Ethyl 3-{4-[3-(N-benzyloxycarbonyl-N-(2-pyridinyl)amino)propyl]-3,4-dihydro-2H-1,4-benzoxazin-7-yl)amino}-3-phenylpropanoate, 9

Compound 7 (m=1, 0.1 g, 0.16 mmol) was dissolved in THF, cooled and treated with 1M boron hydride-tetrahydrofuran complex (0.75 mL, 0.75 mmol). The mixture was refluxed for 3 h, cooled, acidified with 0.5N hydrochloric acid, poured into water and extracted with ethyl acetate. The organic extracts were washed with saturated sodium bicarbonate, dried over sodium sulfate and the solvent evaporated. The residue was purified by flash chromatography, eluting with petroleum ether/ethyl acetate 7:3, to give 0.063 g (65%) of 9 as a yellow oil.

Ethyl 3-{4-[3-(N-(2-pyridinyl)amino)propyl]-3,4-dihydro-2H-1,4-benzoxazin-7-yl)amino}-3-phenylpropanoate, 10

Compound 9 (0.06 g, 0.1 mmol) in acetic acid was cooled to 5–7° C., 30% hydrobromic acid in acetic acid (10 mL) was added and the mixture stirred at room temperature overnight. The solvent was removed, the residue cooled and treated with saturated sodium bicarbonate at 5° C. The aqueous mixture was extracted with dichloromethane. The organic extracts were dried over sodium sulfate, evaporated to small volume and the residue purified by flash chromatography (dichloromethane/methanol 95:5) to give 0.028 g (61%) of 10.

3-{4-[3-(N-(2-pyridinyl)amino)propyl]-3,4-dihydro-2H-1,4-benzoxazin-7-yl)amino}-3-phenylpropanoic acid, 2

To a stirred solution of 10 (0.025 g, 0.54 mmol) in dioxane (12 mL) cooled to 5° C., 2N sodium hydroxide (5 mL) was added and the mixture stirred overnight. The pH was adjusted to neutrality by adding the stoichiometric amount of 2N hydrochloric acid. Silica gel was added to the mixture, the solvent was evaporated and the residue purified by flash chromatography (dichloromethane/methanol/acetic acid 85:15:1) to give 0.017 g (76%) of PHA 513405 as a white solid.

$^1$H-NMR (400 MHz), δ (DMSO-$d_6$): 1.68 (m, 2H, $CH_2$ $\underline{CH_2}CH_2$), 2.58 (m, 2H, $\underline{CH_2}COOH$), 3.00–3.40 (m, 6H, $\underline{CH_2}NHPyr$, 2 $CH_2N$), 4.03 (m, 2H, $CH_2O$), 4.58 (m, 1H, Ph$\underline{CH}NH$), 5.93 (d, 1 H, J=2.4, ArH), 6.00 (dd, 1H, J=2.4, 8.6, ArH), 6.42 (m, 3H, ArH+H-5 pyridine+H-3 pyridine), 7.10–7.40 (m, 6H, PhH+H-4 pyridine), 7.91 (m, 1H, H-6 pyridine).

By analogous procedures the following compounds can be obtained:

3-phenyl-N-{4-[2-(2-pyridinylamino)ethyl]-3,4-dihydro-2H-1,4-benzoxazin-7-yl}-beta-alanine 3-phenyl-N-{4-[4-(2-pyridinylamino)butyl]-3,4-dihydro-2H-1,4-benzoxazin-7-yl}-beta-alanine N-{4-[2-(1H-imidazol-2-ylamino)ethyl]-3,4-dihydro-2H-1,4-benzoxazin-7-yl}-3-phenyl-beta-alanine N-{4-[3-(1H-imidazol-2-ylamino)propyl]-3,4-dihydro-2H-1,4-benzoxazin-7-yl}-3-phenyl-beta-alanine N-{4-[2-(1H-imidazol-2-ylamino)butyl]-3,4-dihydro-2H-1,4-benzoxazin-7-yl}-3-phenyl-beta-alanine 3-(3-pyridinyl)-N-{4-[2-(2-pyridinylamino)ethyl]-3,4-dihydro-2H-1,4-benzoxazin-7-yl}-beta-alanine 3-(3-pyridinyl)-N-{4-[3-(2-pyridinylamino)propyl]-3,4-dihydro-2H-1,4-benzoxazin-7-yl}-beta-alanine 3-(3-pyridinyl)-N-{4-[4-(2-pyridinylamino)butyl]-3,4-dihydro-2H-1,4-benzoxazin-7-yl}-beta-alanine N-{4-[2-(1H-imidazol-2-ylamino)ethyl]-3,4-dihydro-2H-1,4-benzoxazin-7-yl}-3-(3-pyridinyl)-beta-alanine N-{4-[3-(1H-imidazol-2-ylamino)propyl]-3,4-dihydro-2H-1,4-benzoxazin-7-yl}-3-(3-pyridinyl)-beta-alanine N-{4-[4-(1H-imidazol-2-ylamino)butyl]-3,4-dihydro-2H-1,4-benzoxazin-7-yl}-3-(3-pyridinyl)-beta-alanine N-{3-oxo-4-[2-(2-pyridinylamino)ethyl]-3,4-dihydro-2H-1,4-benzoxazin-7-yl}-3-phenyl-beta-alanine N-{3-oxo-4-[4-(2-pyridinylamino)butyl]-3,4-dihydro-2H-1,4-benzoxazin-7-yl}-3-phenyl-beta-alanine N-{4-[2-(1H-imidazol-2-ylamino)ethyl]-3-oxo-3,4-dihydro-2H-1,4-benzoxazin-7-yl}-3-phenyl-beta-alanine N-{4-[3-(1H-imidazol-2-ylamino)propyl]-3-oxo-3,4-dihydro-2H-1,4-benzoxazin-7-yl}-3-phenyl-beta-alanine N-{4-[4-(1H-imidazol-2-ylamino)butyl]-3-oxo-3,4-dihydro-2H-1,4-benzoxazin-7-yl}-3-phenyl-beta-alanine N-{3-oxo-4-[2-(2-pyridinylamino)ethyl]-3,4-dihydro-2H-1,4-benzoxazin-7-yl}-3-(3-pyridinyl)-beta-alanine N-{3-oxo-4-[3-(2-pyridinylamino)propyl]-3,4-dihydro-2H-1,4-benzoxazin-7-yl}-3-(3-pyridinyl)-beta-alanine N-{3-oxo-4-[4-(2-pyridinylamino)butyl]-3,4-dihydro-2H-1,4-benzoxazin-7-yl}-3-(3-pyridinyl)-beta-alanine N-{4-[2-(1H-imidazol-2-ylamino)ethyl]-3-oxo-3,4-dihydro-2H-1,4-benzoxazin-7-yl)-3-(3-pyridinyl)-beta-alanine N-{4-[3-(1H-imidazol-2-ylamino)propyl]-3-oxo-3,4-dihydro-2H-1,4-benzoxazin-7-yl}-3-(3-pyridinyl)-beta-alanine N-{4-[4-(1H-imidazol-2-ylamino)butyl]-3-oxo-3,4-dihydro-2H-1,4-benzoxazin-7-yl}-3-(3-pyridinyl)-beta-alanine either as a free acid or a salt thereof, in particular the hydrochloride or the trifluoroacetate.

EXAMPLE 2

The compound 3-({3-oxo-4-[3-(2-pyridinylamino)propyl]-3,4-dihydro-2H-1,4-benzoxazin-7-yl}oxy)-3-phenylpropanoic acid can be prepared as described in Scheme 3.

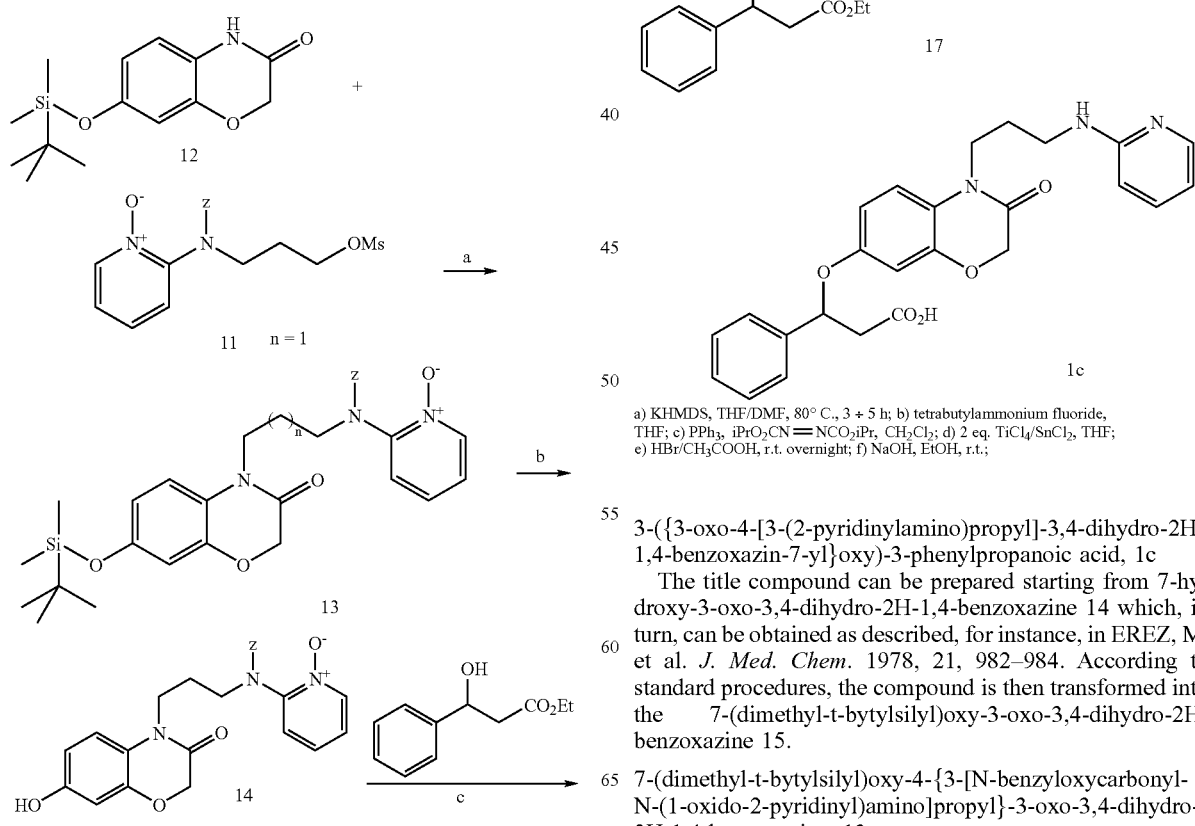

a) KHMDS, THF/DMF, 80° C., 3 + 5 h; b) tetrabutylammonium fluoride, THF; c) PPh₃, iPrO₂CN═NCO₂iPr, CH₂Cl₂; d) 2 eq. TiCl₄/SnCl₂, THF; e) HBr/CH₃COOH, r.t. overnight; f) NaOH, EtOH, r.t.;

3-({3-oxo-4-[3-(2-pyridinylamino)propyl]-3,4-dihydro-2H-1,4-benzoxazin-7-yl}oxy)-3-phenylpropanoic acid, 1c The title compound can be prepared starting from 7-hydroxy-3-oxo-3,4-dihydro-2H-1,4-benzoxazine 14 which, in turn, can be obtained as described, for instance, in EREZ, M. et al. *J. Med. Chem.* 1978, 21, 982–984. According to standard procedures, the compound is then transformed into the 7-(dimethyl-t-bytylsilyl)oxy-3-oxo-3,4-dihydro-2H-benzoxazine 15.

7-(dimethyl-t-bytylsilyl)oxy-4-{3-[N-benzyloxycarbonyl-N-(1-oxido-2-pyridinyl)amino]propyl}-3-oxo-3,4-dihydro-2H-1,4-benzoxazine, 13

To a stirred solution of 12 in tetrahydrofuran and dimethylforamide, cooled to 0° C. under nitrogen atmosphere, potassium hexamethyldisilazide is added and the mixture stirred for 10–15 minutes. Then, a solution of 3-[N-benzyloxycarbonyl-N-(1-oxido-2-pyridinyl)amino]propyl methanesulfonate in tetrahydrofuran is added, the reaction mixture heated at 80° C. for 3 to 5 hours. The solvent is removed, the residue taken up with water, extracted with dichloromethane, the organic fractions washed with aqueous sodium bisulfate followed by sodium bicarbonate solution. After drying over sodium sulfate, the solvent is evaporated and the product is isolated by flash chromatography.

7-hydroxy-4-{3-[N-benzyloxycarbonyl-N-(1-oxido-2-pyridinyl)amino]-propyl}-3-oxo-3,4-dihydro-2H-1,4-benzoxazine, 14

To a solution of 7-(dimethyl-t-bytylsilyl)oxy-4-{3-[N-benzyloxycarbonyl-N-(1-oxido-2-pyridinyl)amino]propyl}-3-oxo-3,4-dihydro-2H-1,4-benzoxazine in tetrahydrofuran is added a solution of tetrabutylammonium fluoride in tetrahydrofuran and the reaction mixture left standing overnight. Then, the solvent is evaporated, and the residue taken up with an aqueous solution of hydrochloric acid, and extracted with dichloromethane. The organic phase is washed with a solution of sodium bicarbonate, then with brine and dried over anhydrous sodium sulfate. Evaporation of the solvent yields the title compound.

Ethyl 3-({3-oxo-4-[3-(N-benzyloxycarbonyl-N-(1-oxido-2-pyridinyl)amino]-propyl-3,4-dihydro-2H-1,4-benzoxazin-7-yl}oxy)-3-phenyl propanoate, 15

To a solution of 7-hydroxy-4-{3-[N-benzyloxycarbonyl-N-(1-oxido-2-pyridinyl)amino]propyl}-3-oxo-3,4-dihydro-2H-1,4-benzoxazine in dichloromethane are added 5 equivalents of tripenylphosphine and 1.1 equivalents of 3-hydroxy-3-phenyl propanoic acid ethyl ester. A solution of 5 equivalents of diisopropyl azodicarboxylate in dichloromethane is added dropwise at room temperature over 1 hour. The reaction mixture is stirred at room temperature for six hours, then the solvent is evaporated and the product isolated by column chromatography.

Ethyl 3-({3-oxo-4-[3-(N-benzyloxycarbonyl-N-(2-pyridinyl)amino]propyl-3,4-dihydro-2H-1,4-benzoxazin-7-yl}oxy)-3-phenylpropanoate, 16

To a solution of titanium (IV) chloride in tetrahydrofuran under nitrogen atmosphere, is added and equimolar amount of stannous chloride dihydrate, and the mixture is stirred 1 hour at room temperature. Then, a solution of ethyl 3-({3-oxo-4-[3-(N-benzyloxycarbonyl-N-(1-oxido-2-pyridinyl)amino]propyl-3,4-dihydro-2H-1,4-benzoxazin-7-yl}oxy)-3-phenylpropanoate is added and the mixture heated 3 hours at 40° C. After evaporation of the solvent, ice and aqueous sodium bicarbonate are added, the mixture extracted with ethyl acetate, and the organic layers are combined and dried over sodium sulphate. The solvent is evaporated and the product is isolated by column chromatography.

Ethyl 3-({3-oxo-4-[3-(N-(2-pyridinyl)amino]propyl-3,4-dihydro-2H-1,4-benzoxazin-7-yl}oxy)-3-phenylpropanoate, 17

A solution of ethyl 3-({3-oxo-4-[3-(N-benzyloxycarbonyl-N-(2-pyridinyl)-amino]propyl-3,4-dihydro-2H-1,4-benzoxazin-7-yl}oxy)-3-phenyl-propanoate in acetic acid is cooled with an ice bath, and a solution of 30% hydrobromic acid in acetic acid is added. The mixture is stirred at room temperature overnight. The solvent is removed under reduced pressure, the residue cooled and treated with saturated sodium bicarbonate. The aqueous mixture is extracted with dichloromethane. The organic extracts are dried over sodium sulfate, evaporated to small volume and the product is purified by flash chromatography.

3-({3-oxo-4-[3-(2-pyridinylamino)propyl]-3,4-dihydro-2H-1,4-benzoxazin-7-yl}oxy)-3-phenylpropanoic acid, 1c A solution of ethyl 3-({3-oxo-4-[3-(N-(2-pyridinyl)amino-propyl]-3,4-dihydro-2H-1,4-benzoxazin-7-yl}oxy)-3-phenylpropanoate in ethanol is treated with an equimolar amount of 1N sodium hydroxide solution. The mixture is stirred at room temperature overnight. Then, the pH is brought to neutrality with 1N hydrochloric acid, the solvent is evaporated and the residue is purified by filtration through a small pad of silica gel, eluting with a mixture of dichloromethane, methanol and acetic acid.

By analogous procedures the following compounds can be obtained:
3-({3-oxo-4-[3-(1H-imidazol-2-ylamino)propyl]-3,4-dihydro-2H-1,4-benzoxazin-7-yl}oxy)-3-phenylpropanoic acid;
3-({3-oxo-4-[4-(2-pyridinylamino)butyl]-3,4-dihydro-2H-1,4-benzoxazin-7-yl}oxy)-3-phenylpropanoic acid;
3-({3-oxo-4-[4-(1H-imidazol-2-ylamino)butyl]-3,4-dihydro-2H-1,4-benzoxazin-7-yl}oxy)-3-phenylpropanoic acid;
3-({3-oxo-4-[3-(2-pyridinylamino)propyl]-3,4-dihydro-2H-1,4-benzoxazin-7-yl}oxy)-3-(3-pyridinyl)propanoic acid;
3-({3-oxo-4-[4-(2-pyridinylamino)butyl]-3,4-dihydro-2H-1,4-benzoxazin-7-yl}oxy)-3-(3-pyridinyl)propanoic acid;
3-({3-oxo-4-[3-(1H-imidazol-2-ylamino)propyl]-3,4-dihydro-2H-1,4-benzoxazin-7-yl}oxy)-3-(3-pyridinyl)propanoic acid;
3-((3-oxo-4-[4-(1H-imidazol-2-ylamino)butyl]-3,4-dihydro-2H-1,4-benzoxazin-7-yl}oxy)-3-(pyridinyl)propanoic acid;

EXAMPLE 3

3-({3-oxo-4-[3-(2-pyridinylamino)propyl]-3,4-dihydro-2H-1,4-benzoxazin-7-yl}sulfanyl)-3-phenylpropanoic acid, The compound can be synthesized as described in Scheme 4.

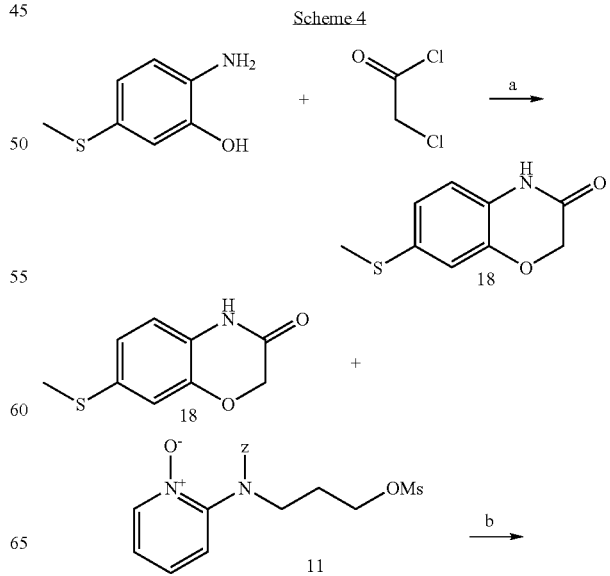

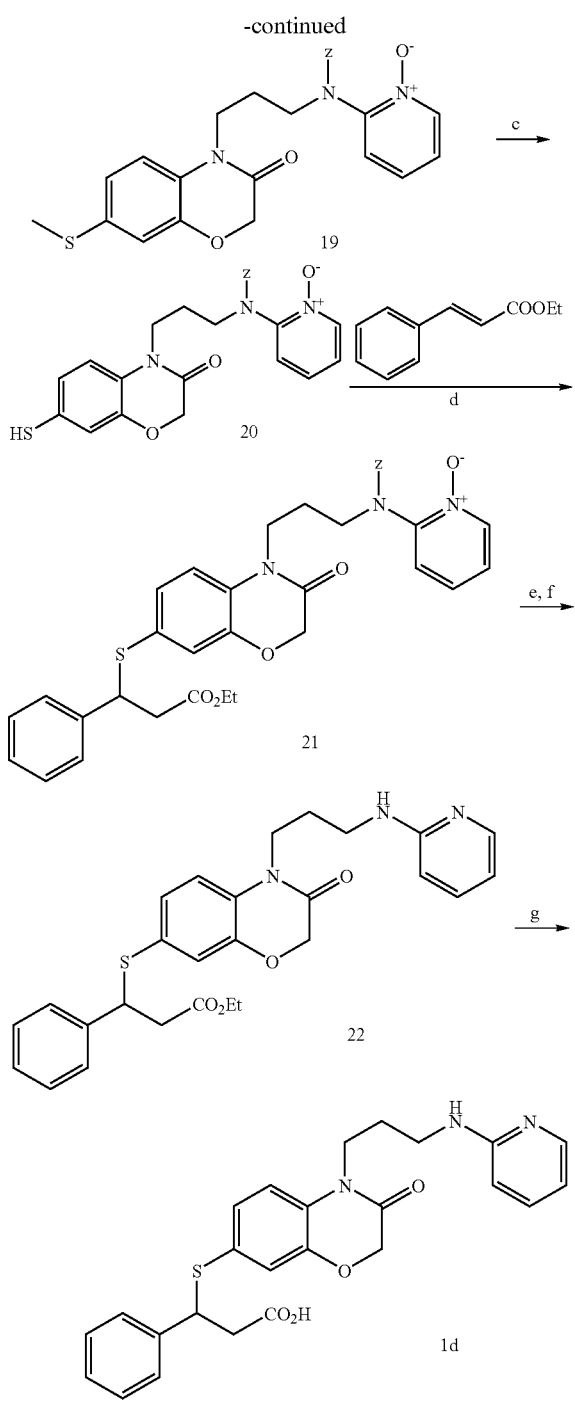

a) TEA, DMAP, CH₂Cl₂, reflux; b) KHMDS, THF/DMF, 80° C., 3 ÷ 5 h;
c) TFAA, MCPBA; d) DBU, DMF; e) TiCl₄/SnCl₂; f) HBr/CH₃COOH,
r.t. overnight; g) NaOH, EtOH, r.t.;

7-methylthio-4-{3-[N-benzyloxycarbonyl-N-(1-oxido-2-pyridinyl)amino]-propyl}-3-oxo-3,4-dihydro-2H-1,4-benzoxazine, 19

The synthesis is performed, as depicted in Scheme 4, according to the procedure described for derivative 4, by condensing the commercially available, 2-amino-5-(methylthio)phenol with chloroacetyl chloride and subsequently alkylating the benzoxazinone 18 with compound 11, using potassium hexamethyldisilazide as a base in tetrahydrofuran/dimethylformamide at 80° C., yielding compound 19.

7-thio-4-{3-[N-benzyloxycarbonyl-N-(1-oxido-2-pyridinyl)amino]propyl}-3-oxo-3,4-dihydro-2H-1,4-benzoxazine, 20

The demethylation of the methylthio function is performed by treatment of compound 19 with m-cloro-perbenzoic acid and trifluorocetic anhydride, according to a procedure described in the literature (YOUNG, R. N.; GAUTHIER, J. Y.; COOMBS, W.; *Tetrahedron Lett.*, 1984, 25, 1753).

Ethyl 3-[(4-{3-[N-benzyloxycarbonyl-N-(1-oxido-2-pyridinyl)amino]propyl}-3-oxo-3,4-dihydro-2H-1,4-benzoxazin-7-yl)sulfanyl]-3-phenylpropanoate 21

To a solution of 7-thio-4-{3-[N-benzyloxycarbonyl-N-(1-oxido-2-pyridinyl)-amino]propyl}-3-oxo-3,4-dihydro-2H-1,4-benzoxazine in dimethylformamide is added an equimolar amount of ethyl trans-cinnamate and a 0.05 equivalents of diazabicycloundecene (DBU). The reaction mixture is stirred at room temperature for 12 hours. The solvent is evaporated and the product is purified by flash chromatography.

Ethyl 3-({3-oxo-4-[3-(2-pyridinylamino)propyl]-3,4-dihydro-2H-1,4-benzoxazin-7-yl}sulfanyl)-3-phenylpropanoate, 22

To a solution of titanium (IV) chloride in tetrahydrofuran under nitrogen atmosphere, is added and equimolar amount of stannous chloride dihydrate, and the mixture is stirred 1 hour at room temperature. Then, a solution of ethyl 3-[(4-{3-[N-benzyloxycarbonyl-N-(1-oxido-2-pyridinyl)amino]propyl}-3-oxo-3,4-dihydro-2H-1,4-benzoxazin-7-yl)sulfanyl]-3-phenylpropanoate is added and the mixture heated 3 hours at 40° C. After evaporation of the solvent, ice and aqueous sodium bicarbonate are added, the mixture extracted with ethyl acetate, and the organic layers are combined and dried over sodium sulfate. The solvent is evaporated and ethyl 3-[(4-{3-[N-benzyloxycarbonyl-N-(2-pyridinyl)amino]-propyl}-3-oxo-3,4-dihydro-2H-1,4-benzoxazin-7-yl)sulfanyl]-3-phenylpropanoate is isolated by column chromatography. A solution of ethyl 3-[(4-{3-[N-benzyloxycarbonyl-N-(2-pyridinyl)amino]-propyl}-3-oxo-3,4-dihydro-2H-1,4-benzoxazin-7-yl)sulfanyl]-3-phenylpropanoate in acetic acid is treated with a solution of 30% hydrobromic acid in acetic acid at room temperature overnight. The solvent is evaporated under reduced pressure, and the residue is treated with a saturated sodium bicarbonate solution. The aqueous mixture is extracted with dichloromethane. The organic extracts are dried over sodium sulfate, evaporated to small volume and the product is purified by flash chromatography 3-({3-oxo-4-[3-(2-pyridinylamino)propyl]-3,4-dihydro-2H-1,4-benzoxazin-7-yl}sulfanyl)-3-phenylpropanoic acid 1d A solution of ethyl 3-({3-oxo-4-[3-(2-pyridinylamino)propyl]-3,4-dihydro-2H-1,4-benzoxazin-7-yl}sulfanyl)-3-phenylpropanoate in ethanol is treated with an equimolar amount of 1N sodium hydroxide solution. The mixture is stirred at room temperature overnight. Then, the pH is brought to neutrality with 1N hydrochloric acid, the solvent is evaporated under reduced pressure and the residue is purified by filtration through a small pad of silica gel, eluting with a mixture of dichloromethane, methanol and acetic acid.

By analogous procedures the following compounds can be obtained:

3-({3-oxo-4-[4-(2-pyridinylamino)butyl]-3,4-dihydro-2H-1,4-benzoxazin-7-yl}sulfanyl)-3-phenylpropanoic acid;

3-({3-oxo-4-[3-(1H-imidazol-2-ylamino)propyl]-3,4-dihydro-2H-1,4-benzoxazin-7-yl}sulfanyl)-3-phenylpropanoic acid;

3-({3-oxo-4-[4-(1H-imidazol-2-ylamino)butyl]-3,4-dihydro-2H-1,4-benzoxazin-7-yl}sulfanyl)-3-phenylpropanoic acid;

3-({3-oxo-4-[3-(2-pyridinylamino)propyl]-3,4-dihydro-2H-1,4-benzoxazin-7-yl}sulfanyl)-3-(3-ppyridinyl)propanoic acid;

3-({3-oxo-4-[4-(2-pyridinylamino)butyl]-3,4-dihydro-2H-1,4-benzoxazin-7-yl}sulfanyl)-3-(3-pyridinyl)propanoic acid;

3-({3-oxo-4-[3-(1H-imidazol-2-ylamino)propyl]-3,4-dihydro-2H-1,4-benzoxazin-7-yl}sulfanyl)-3-(3-pyridinyl)propanoic acid;

3-({3-oxo-4-[4-(1H-imidazol-2-ylamino)butyl]-3,4-dihydro-2H-1,4-benzoxazin-7-yl}sulfanyl)-3-(3-pyridinyl)propanoic acid;

EXAMPLE 4

4-{3-Oxo-4-[3-(pyridin-2-ylamino)-propyl]-3,4-dihydro-2H-1,4-benzoxazin-7-yl}-3-phenylbutanoic acid, 1e The compound can be synthesised as described in Scheme 5.

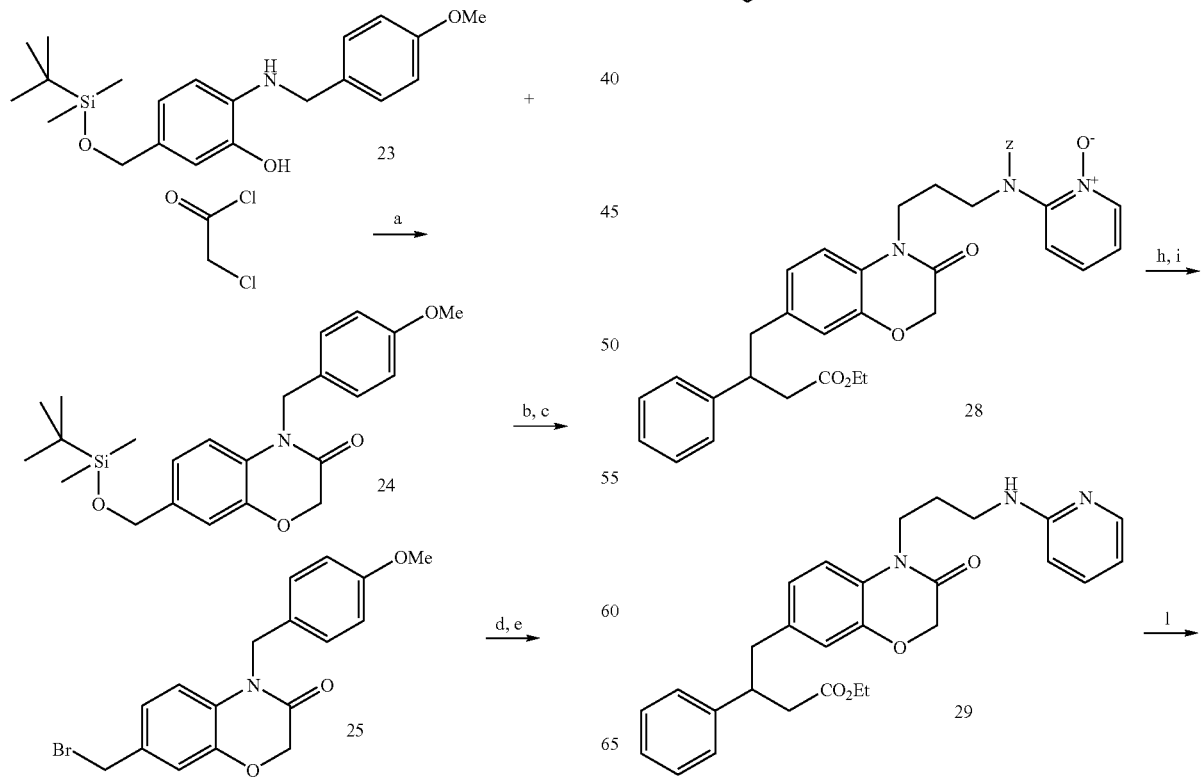

-continued

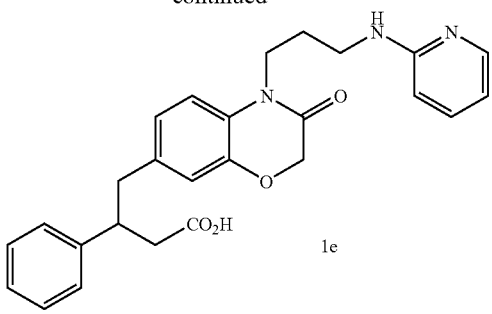

1e a) TEA, DMAP, CH₂Cl₂, reflux; b) tetrabutylammonium fluoride, THF;
c) CBr₄, PPh₃, DEAD, CH₂Cl₂; d) Mg, Et₂O; e) CuI, tetramethylene
diamine, THF, -78° C., then add Grignard reagent, trimethylsilyl chloride,
ethyl cinnamate; f) 10% Pd/C, H₂, EtOH; g) potassium hexamethyldisilazide,
THF/DMF, 80° C., 5 h; h) TiCl₄/SnCl₂, THF; i) HBr/CH₃COOH, r.t. overnight;
l) NaOH, EtOH, r.t.;

Compound 23 is easily prepared by protection of the hydroxyl group of 5-hydroxymethyl-2-(4-methoxybenzylamino) phenol, which, in turn, is prepared as described in YADAGIRI, B., LOWN, J. W. *Synthetic Communications* 1990, 20, 175–181.

7-(dimethyl-t-butylsilyl)oxymethyl-4-p-methoxybenzyl-3-oxo-3,4-dihydro-2H-1,4-benzoxazine, 24

To a stirred solution of 5-(dimethyl-t-butylsilyl)oxymethyl-2-(4-methoxybenzylamino) phenol in anhydrous dichloromethane, triethylamine and dimethylaminopyridine at 0° C. and under nitrogen atmosphere, chloroacetyl-chloride is added. The mixture is refluxed for 10 h, poured into aqueous sodium bisulfate, extracted with dichloromethane and the product isolated by flash chromatography.

7-bromomethyl-4-p-methoxybenzyl-3-oxo-3,4-dihydro-2H-1,4-benzoxazine, 25

A solution of 7-(dimethyl-t-butylsilyl)oxymethyl-4-p-methoxybenzyl-3-oxo-3,4-dihydro-2H-1,4-benzoxazine in tetrahydrofuran is treated with a solution of tetrabutylammonium fluoride in tetrahydrofuran and the reaction mixture left standing overnight. The solvent is evaporated, the residue is treated with aqueous hydrochloric acid and extracted with dichloromethane. The organic phase is washed with a solution of sodium bicarbonate, brine and then dried on sodium sulfate. Evaporation of the solvent and filtration through a small pad of silica gel yields the pure 7-hydroxymethyl-4-p-methoxybenzyl-3-oxo-3,4-dihydro-2H-1,4-benzoxazine. To a solution of 7-hydroxymethyl-4-p-methoxybenzyl-3-oxo-3,4-dihydro-2H-1,4-benzoxazine in dichloromethane is added triphenylphosphine and carbonium tetrabromide. Then a solution of diethyl azodicarboxylate in dichloromethane is added dropwise and the reaction mixture stirred at room temperature for 6 hours. The solvent is evaporated and the product isolated by flash chromatography.

Ethyl 4-[3-oxo-4-[p-methoxybenzyl]-3,4-dihydro-2H-1,4-benzoxazin-7-yl]-3-phenylbutanoate, 26

To a suspension of CuI in dry tetrahydrofuran under argon are added 1.1 equivalents of tetramethylene diamine and the reaction mixture stirred at room temperature for 15 minutes. The solution is cooled to -78° C. and the Grignard reagent prepared from 7-bromomethyl-4-p-methoxybenzyl-3-oxo-3,4-dihydro-2H-1,4-benzoxazine is added and the reaction mixture stirred for 15 minutes. Then, 2 equivalents of trimethylsilyl chloride and a solution of ethyl cinnamate in tetrahydrofuran are added and the reaction mixture is stirred while the temperature is allowed to rise to -30° C. After 18 hours the reaction is poured into a solution of ammonium chloride and ammonium hydroxide and extracted with dichloromethane. The extracts are washed with water, dried over sodium sulfate, evaporated and the product isolated by flash chromatography.

Ethyl 4-[3-Oxo-3,4-dihydro-2H-1,4-benzoxazin-7-yl]-3-phenylbutanoate, 27

To a solution of ethyl 4-[3-oxo-4-[p-methoxybenzyl]-3,4-dihydro-2H-1,4-benzoxazin-7-yl]-3-phenylbutanoate in ethanol is added 10% Pd/C and the compound hydrogenated in a Parr apparatus. Evaporation of the solvent yields the title compound.

Ethyl 3-[(4-{3-[N-benzyloxycarbonyl-N-(1-oxido-2-pyridinyl)amino]propyl}-3-oxo-3,4-dihydro-2H-1,4-benzoxazin-7-yl)]-3-phenylbutanoate, 28

To a stirred solution of ethyl 4-[3-oxo-3,4-dihydro-2H-1,4-benzoxazin-7-yl]-3-phenylbutanoate in tetrahydrofuran and dimethylforamide, cooled to 0° C. under nitrogen atmosphere, potassium hexamethyldisilazide is added and the mixture stirred for 10–15 minutes. Then, a solution of 3-[N-benzyloxycarbonyl-N-(1-oxido-2-pyridinyl)amino] propyl methanesulfonate in tetrahydrofuran is added, the reaction mixture heated at 80° C. for 3 to 5 hours. The solvent is removed, the residue taken up with water, extracted with dichloromethane, the organic fractions washed with aqueous sodium bisulfate followed by sodium bicarbonate solution. After drying over sodium sulfate, the solvent was evaporated and the product is isolated by flash chromatography.

Ethyl 3-[(4-{3-[(2-pyridinyl)amino]propyl}-3-oxo-3,4-dihydro-2H-1,4-benzoxazin-7-yl)]-3-phenylbutanoate, 29

To a solution of titanium (IV) chloride in tetrahydrofuran under nitrogen atmosphere, is added an equimolar amount of stannous chloride dihydrate, and the mixture is stirred 1 hour at room temperature. Then, a solution of ethyl 3-[(4-{3-[N-benzyloxycarbonyl-N-(1-oxido-2-pyridinyl)amino]propyl}-3-oxo-3,4-dihydro-2H-1,4-benzoxazin-7-yl)]-3-phenylbutanoate is added and the mixture heated 3 hours at 40° C. After evaporation of the solvent, ice and aqueous sodium bicarbonate are added, the mixture extracted with ethyl acetate, and the organic layers are combined and dried over sodium sulfate. The solvent is evaporated, the residue is dissolved in ethanol, 10% Pd/C is added and the compound hydrogenated in a Parr apparatus. The solvent is then evaporated and the product is isolated by column chromatography.

4-{3-Oxo-4-[3-(pyridin-2-ylamino)-propyl]-3,4-dihydro-2H-1,4-benzoxazin-7-yl}-3-phenylbutanoic acid, 1e A solution of ethyl 3-[(4-{3-[(2-pyridinyl)amino]propyl}-3-oxo-3,4-dihydro-2H-1,4-benzoxazin-7-yl)]-3-phenylbutanoate in ethanol is treated with an equimolar amount of 1N sodium hydroxide solution. The mixture is stirred at room temperature overnight. Then, the pH is brought to neutrality with 1N hydrochloric acid, the solvent is evaporated under reduced pressure and the residue is purified by filtration through a small pad of silica gel, eluting with a mixture of dichloromethane, methanol and acetic acid.

By analogous procedures the following compounds can be obtained:
4-{3-oxo-4-[4-(pyridin-2-ylamino)-butyl]-3,4-dihydro-2H-1,4-benzoxazin-7-yl}-3-phenylbutanoic acid;
4-{3-oxo-4-[3-(1H-imidazol-2-ylamino)-propyl]-3,4-dihydro-2H-1,4-benzoxazin-7-yl}-3-phenylbutanoic acid;

4-{3-oxo-4-[4-(1H-imidazol-2-ylamino)-butyl]-3,4-dihydro-2H-1,4-benzoxazin-7-yl}-3-phenylbutanoic acid;

4-{3-oxo-4-[4-(pyridin-2-ylamino)-butyl]-3,4-dihydro-2H-1,4-benzoxazin-7-yl}-3-(3-pyridinyl)butanoic acid;

4-{3-oxo-4-[3-(1H-imidazol-2-ylamino)-propyl]-3,4-dihydro-2H-1,4-benzoxazin-7-yl}-3-(3-pyridinyl)butanoic acid;

4-{3-oxo-4-[4-(1H-imidazol-2-ylamino)-butyl]-3,4-dihydro-2H-1,4-benzoxazin-7-yl}-3-(3-pyridinyl)butanoic acid;

Pharmacology

The compounds of the invention are selective integrin receptor inhibitors or antagonists, and in particular they are inhibitors or antagonists of the $\alpha_v\beta_3$ integrin receptor. The specific inhibiting or antagonist activity of the compounds of the invention is shown for instance by the fact that they are active in in vitro solid phase $\alpha_v\beta_3$-vitronectin binding assay, as described below.

$\alpha_v\beta_3$-vitronectin Binding Assay

A solid phase assay for the study of $\alpha_v\beta_3$-vitronectin binding was set up on the basis of already published methods (WONG et al., *Molecular Pharmacology* 50: 529–537, 1996; Brooks et al., Cell 85: 683–693, 1996). The human $\alpha_v\beta_3$ integrin was diluted into coating buffer (CB) containing 150 mM NaCl, 1 mM CaCl$_2$, 1 mM MgCl$_2$, 1 mM MnCl$_2$, 20 mM TRIS, pH 7.4 at a concentration of 1.5 µg/ml. Into 96-well plates, 50 µl of the diluted integrin were added and allowed to bind to the plate walls overnight at 4° C. Next day, the assay plates were emptied and 100 µl of blocking buffer (CB buffer with 3% BSA) were added to each well for 45 min at 37° C. After the incubation, the plates were washed three times with 100 µl assay buffer (AB, CB buffer with 0.1% BSA); serial 1:1 dilution (25 µl/well) of the test compounds were added to the plates, starting from 10 mM solutions in 100% DMSO diluted to 100 µM in AB. The binding reaction was started by addition (25 µl/well) of 10 nM biotinylated vitronectin (final concentration: 5 nM), and lasted 30 min at 37° C. The concentration range of the tested compounds spanned from 50 to 0.0005 µM. At the end of the co-incubation, the assay plates were washed as before and 70 µl of a 1:1000 AB dilution of peroxydase-conjugated streptavidin were added per well and were allowed to react for 45 min at 37° C. Then, the plates were washed as described and 50 µl of ready to use Turbo-TMB substrate for peroxydase were added to each well. After 30 minutes incubation at room temperature, the color development was stopped with 50 µl sulphuric acid 0.38 M and the plates were read at a wavelength of 450 nm with a Packard plate reader. The values obtained were analyzed by four parameters curve fit in the computer program GraphPad Prism, after normalization by a maximum binding control (Bmax) detected in wells where no competitor was added, and a minimum binding control (NSB) detected in wells where no integrin was coated. Under standard assay conditions, A$_{450}$ was never under 1.0 for Bmax, and around 0.15 for NSB. The computerized algorithm gave the concentration of compound needed to inhibit the maximum binding by 50% (IC$_{50}$ value): for those compounds that did not inhibit this binding by 50% at the highest concentration tested, IC$_{50}$ value was reported as being greater then the highest concentration tested. As a positive control, increasing doses of a peptide containing the RGD sequence was added to each plate: IC$_{50}$ value of this molecule was 120 nM.

Materials

Human vitronectin receptor ($\alpha_v\beta_3$) was purified from human placenta (PYTELA et al, Methods in Enzymology, 144: 475–489, 1987). Turbo-TMB was from PIERCE (34022). BSA (A4503), Vitronectin (V8379), RGD peptide (G4144) and all generic reagents were from SIGMA. Vitronectin was biotinylated according to the procedure indicated in the NHS biotinylation kit from PIERCE (21420). Horseradish peroxydase-streptavidin was from Amersham (RPN1231). 96-well plates were from Costar (#3690, EIA/RIA plate, ½ area flat bottom, high binding).

$\alpha_{IIb}\beta_3$-Fibrinogen Binding Assay

A solid phase assay for the study of $\alpha_{IIb}\beta_3$-fibrinogen binding was set up according to the method described for $\alpha_v\beta_3$. $\alpha_{IIb}\beta_3$ integrin was diluted into coating buffer (CB) containing 150 mM NaCl, 1 mM CaCl$_2$, 1 mM MgCl$_2$, 1 mM MnCl$_2$, 20 mM TRIS, pH 7.4 at a concentration of 3 µg/ml. Into 96-well plates, 50 µl of the diluted integrin were added and allowed to bind to the plate walls overnight at 4° C. Next day, the assay plates were emptied and 100 µl of blocking buffer (CB buffer with 3% BSA) were added to each well for 45 min at 37° C. After the incubation, the plates were washed three times with 100 µl assay buffer (AB, CB buffer with 0.1% BSA); serial 1:1 dilution (25 µl/well) of the test compounds were added to the plates, starting from 10 mM solutions in 100% DMS0 diluted to 100 µM in AB. The binding reaction was started by addition (25 µl/well) of 20 nM biotinylated fibrinogen (final concentration: 10 nM), and lasted 30 min at 37° C. The concentration range of the tested compounds spanned from 50 to 0.0005 µM. At the end of the co-incubation, the assay plates were washed as before and 70 µl of a 1:1000 AB dilution of peroxydase-conjugated streptavidin were added per well and were allowed to react for 45 min at 37° C. Then, the plates were washed as described and 50 µl of ready to use Turbo-TMB substrate for peroxydase were added to each well. After 30 minutes incubation at room temperature, the color development was stopped with 50 µl sulphuric acid 0.38 M and the plates were read at a wavelength of 450 nm with a Packard plate reader. The values obtained were analyzed by four parameters curve fit with the computer program GraphPad Prism, after normalization by a maximum binding control (Bmax) detected in wells where no competitor was added, and a minimum binding control (NSB) detected in wells where no integrin was coated. Under standard assay conditions, A$_{450}$ was never under 0.8 for Bmax, and around 0.15 for NSB. The computerized algorithm gave the concentration of compound needed to inhibit the maximum binding by 50% (IC$_{50}$ value): for those compounds that did not inhibit this binding by 50% at the highest concentration tested, IC$_{50}$ value was reported as being greater then the highest concentration tested. As a positive control, increasing doses of a peptide containing the RGD sequence was added to each plate: IC$_{50}$ value of this molecule was 2.3 µM for $\alpha_{IIb}\beta_3$-fibrinogen binding.

Materials

Human fibrinogen receptor ($\alpha_{IIb}\beta_3$) was purified from human platelets ((Pytela et al, Methods in Enzymology, 144: 475–489, 1987). Turbo-TMB was from PIERCE (34022). BSA (A4503), fibrinogen (F4883), RGD peptide (G4144) and all generic reagents were from SIGMA. Fibrinogen was biotinylated according to the procedure indicated in the NHS biotinylation kit from PIERCE (21420). Horseradish peroxydase-streptavidin was from Amersham (RPN1231). 96-well plates were from Costar (#3690, EIA/RIA plate, ½ area flat bottom, high binding).

For example, compound N-{3-oxo-4-[3-(2-pyridinylamino)propyl]-3,4-dihydro-2H-1,4-benzoxazin-7-yl}-3-phenyl-beta-alanine, when tested in $\alpha_v\beta_3$-vitronectin and $\alpha_{IIb}\beta_3$-fibrinogen biding assays, gave the following activity data:

$\alpha_v\beta_3$ (IC$_{50}$ µmol)=0.011±0.004

$\alpha_{IIb}\beta_3$ (IC$_{50}$ µmol)=18

These test data show that compound N-{3-oxo-4-[3-(2-pyridinylamino)-propyl]-3,4-dihydro-2H-1,4-benzoxazin-7-yl}-3-phenyl-beta-alanine acid is endowed with high selective $\alpha_v\beta_3$ inhibiting activity. In fact, the ratio between $\alpha_{IIb}\beta_3$ and $\alpha_v\beta_3$ inhibiting activity is about 1,000.

In view of their high selective $\alpha_v\beta_3$ inhibiting or antagonizing activity, the compounds of the invention can be used in medicine in treating conditions mediated by the $\alpha_v\beta_3$ integrin. Accordingly, the compounds of the invention are useful for instance for treating various conditions or disease states including osteoporosis, humoral hypercalcemia of malignancy, Paget's disease, tumor metastasis, solid tumor growth (neoplasia), angiogenesis including tumor angiogenesis, retinopathy including diabetic retinopathy, arthritis including rheumatoid arthritis, psoriasis, periodontal disease, smooth muscle cell migration and restenosis in a mammal in need of such treatment. Additionally, such pharmaceutical agents are useful as antiviral agents, and antimicrobials.

According to a preferred object of the invention the $\alpha_v\beta_3$ inhibiting activity results in an anticancer therapy having increased effectiveness in controlling, i.e., slowing, interrupting, arresting, stopping or reversing, the neoplasm formation.

The compounds of the invention can be administered in a variety of dosage forms, e.g. orally, in the form of tablets, capsules, sugar- or film-coated tablets, liquid solutions or suspensions; rectally, in the form of suppositories; parenterally, e.g. intramuscularly, or by intravenous injection of infusion; or topically.

The dosage regimen for the compounds and/or compositions containing the compounds is based on a variety of factors, including the type, age, weight, sex and medical condition of the patent; the severity of the condition; the route of administration; and the activity of the particular compound employed. Thus the dosage regime may vary widely. Dosage levels of the order from about 0.01 mg to about 1000 mg per kilogram of body weight per day are useful in the treatment of the above-indicated conditions and more preferably of the order from about 0.01 mg to about 100 mg/kg of body weight. For instance, the dosage adopted for oral administration to adult humans for compound PHA 509055 may range from about 0.01 mg to about 800 mg/kg of body weight per day and more preferably of the order from about 0.01 mg to about 750 mg/kg body weight.

When given parenterally a suitable daily dose for instance for compound PHA 509055 would typically be about 0.01 to 100 mg/kg body weight injected per day in multiple doses depending on the factors listed above and more preferably from about 0.01 mg to about 10 mg/kg body weight.

The invention includes pharmaceutical compositions comprising a compound of formula (I) or a pharmaceutically acceptable salt thereof in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate, effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example by means of mixing, granulating, tabletting, sugar-coating or film-coating processes.

The liquid dispersion for oral administration may be, e.g., syrups, emulsions and suspensions.

The syrup may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

The solutions for intravenous injections or infusion may contain as carrier, for example, sterile water or, preferably, they may be in the form of sterile aqueous, isotonic saline solutions.

The suppositories may contain, together with the active compound, a pharmaceutically acceptable carrier, e.g. cocoa-butter, polyethylene glycol, a polyoxyethylene sorbitan fatty acid ester surfactant or lecithin.

Compositions for topical application, e.g. creams, lotions or pastes, can be prepared by admixing the active ingredient with a conventional oleaginous or emulsifying excipient.

The following formulation examples illustrate but do not limit the invention.

EXAMPLE 1

Capsules, each dosed at 0.200 g and containing 20 mg of the active substance can be prepared.

Composition for 500 capsules:

| | |
|---|---|
| N-{3-oxo-4-[3-(2-pyridinylamino)propyl]-3,4-dihydro-2H-1,4-benzoxazin-7-yl}-3-phenyl-beta-alanine | 10 g |
| Lactose | 80 g |
| Corn starch | 5 g |
| Magnesium stearate | 5 g |

This formulation is encapsulated in two-piece hard gelatin capsules and dosed at 0.200 g for each capsule.

EXAMPLE 2

Tablets, each weighing 0.150 g and containing 25 mg of the active substance, can be manufactured as follows.
Composition for 10,000 tablets:

| | |
|---|---|
| 3-phenyl-N-{4-[3-(2-pyridinylamino)propyl]-3,4-dihydro-2H-1,4-benzoxazin-7-yl}-beta-alanine | 250 g |
| Lactose | 800 g |
| Corn starch | 415 g |
| Talc powder | 30 g |
| Magnesium stearate | 5 g |

The 3-phenyl-N-{4-[3-(2-pyridinylamino)propyl]-3,4-dihydro-2H-1,4-benzoxazin-7-yl}-beta-alanine, the lactose and half the corn starch are mixed; the mixture is then forced through a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate are added, carefully mixed and processed into tablets.

EXAMPLE 3

Intravenous Infusion 1–10 mg/ml.

An intravenous infusion pharmaceutical preparation can be manufactured by dissolving 50 mg of N-{3-oxo-4-[3-(2-pyridinylamino)propyl]-3,4-dihydro-2H-1,4-benzoxazin-7-yl}-3-phenyl-beta-alanine in water for injection (1000 ml) and sealing glass ampoules of 1–10 ml. Prior to infusion, the obtained solution can be diluted according to the common practice, and stored and/or delivered in glass, polypropylene, polyolefin or polyethylene-lined equipment.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, anti-metabolite agents, hormonal agents, immunological agents, interferon-type agents, cyclooxygenase inhibitors (e.g. COX-2 inhibitors), metallomatrix-protease inhibitors, telomerase inhibitors, tyrosine kinase inhibitors, anti-growth factor receptor agents, anti-HER agents, anti-EGFR agents, anti-angiogenesis agents, farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like. As an example, the compounds of the invention can be administered in combination with one or more chemotherapeutic agents such as, for instance, taxane, taxane derivatives, encapsulated taxanes, CPT-11, camptothecin derivatives, anthracycline glycosides, e.g., doxorubicin, idarubicin, epirubicin, etoposide, navelbine, vinblastine, carboplatin, cisplatin, estramustine, celecoxib, parecoxib, rofecoxib, valecoxib, JTE 5222, Sugen SU-5416, Sugen SU-6668, Herceptin, and the like, optionally within liposomal formulations thereof. If formulated as a fixed dose, such combination products employ the compounds of this invention within the dosage range described above and the other pharmaceutically active agent within the approved dosage range.

Compounds of formula (I) may be used sequentially with known anticancer agents when a combination formulation is inappropriate.

The object of the present invention is to provide the use of a compound of formula (I), as herein defined, or a pharmaceutically acceptable salt thereof, in the preparation of a medicament having $\alpha_v\beta_3$ integrin inhibiting or antagonizing activity for controlling the growth of the neoplasm in a method additionally comprising the administration of an antitumor agent.

The combination preparation according to the invention can also include combination packs or compositions in which the constituents are placed side by side and can therefore be administered simultaneously, separately or sequentially to one and the same human being. Accordingly, the antineoplastic agent and a compound according to the present invention may be present within a single or distinct container means.

In the combined preparations, pharmaceutical compositions and methods of treating, according to the present invention, the antineoplastic agent may comprise 1 to 4, preferably 1, 2 or 3, antineoplastic drugs, in particular a single antineoplastic drug.

As used herein, "controlling the growth" of the neoplasm refers to slowing, interrupting, arresting or stopping its growth and it does not necessarily indicate a total elimination of the neoplasm. It is believed that prolonging the survivability of a patient, beyond being a significant advantageous effect in and of itself, also indicates that the condition is beneficially controlled to some extent.

The term "antineoplastic agent" is meant to comprise both a single antineoplastic cytotoxic drug and "cocktails", i.e. mixtures of such drugs, according to the clinical practice.

As used herein, the term "effective antineoplastic amount" refers to an amount which is effective, upon single or multiple dose administration to the patient, in controlling the growth of the neoplasm or in prolonging the survivability of the patient beyond that expected in the absence of such treatment.

In effecting treatment of a patient afflicted with a disease state described above a compound of formula (I) of the invention can be administered in any form or mode which makes the compound bioavailable in effective amounts, including oral and parenteral routes. For example, it can be administered orally, subcutaneously, intraperitoneally, intramuscularly, intravenously, transdermally, and the like. Oral or intramuscular administration is generally preferred. One skilled in the art of preparing formulations can readily select the proper form and mode of administration depending upon the particular circumstances, including the disease state to be treated, the stage of the disease, the form of administration of the selected cytotoxic agent and the manner of co-administration selected.

The selected antineoplastic agent can be administered by the appropriate route and dosing schedule as is well known and accepted for the particular agent. For example, epirubicin, doxorubicin, idarubicin, paclitaxel, docetaxel, 5-fluorouracil, cyclophosphamide and vinblastine can be administered intravenously. Idarubicin and cyclophosphamide can also be given orally.

The invention claimed is:

1. A compound of the formula (I)

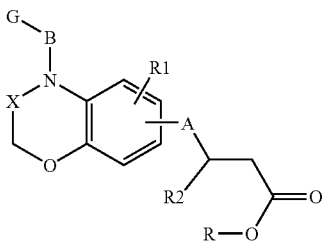

or a pharmaceutically acceptable salt of the compound, or ester of the compound, wherein:

G is selected from the group consisting of a) 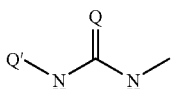

b) 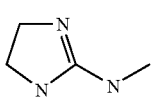

c) 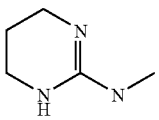

d) 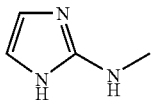

e) 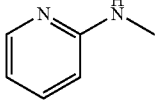

f) 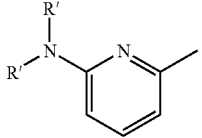

g) 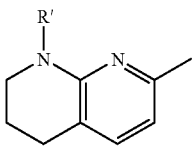

where Q is selected from the group consisting of NH and O, Q' is selected from the group consisting of H, $C_1$–$C_6$ alkyl, phenyl and phenyl-$C_1$–$C_4$-alkyl, and R' is selected from the group consisting of H and $C_1$–$C_4$ alkyl;

B is $(CH_2)_mY$, wherein m=1,2,3, and Y is $CH_2$;

X is selected from the group consisting of $CH_2$ and C=O;

R1 is selected from the group consisting of H, $C_1$–$C_4$ alkyl, $C_1$–$C_4$ alkoxy, OH, halogen, and $CF_3$;

A is selected from the group consisting of $CH_2$, NH, O, and $S(O)_n$ wherein n is zero, 1 or 2;

R2 is selected from the group consisting of phenyl, naphthyl, pyridine, pyrazine, pyridazine, pyrimidine, thiophene, pyrrole, pyrazole, imidazole, oxazole and isoxazole, unsubstituted or optionally substituted with one to three substituents independently selected from the group consisting of H, $C_1$–$C_4$ alkyl, $C_1$–$C_4$ alkoxy, OH, halogen, and $CF_3$; and R is selected from the group consisting of hydrogen, $C_1$–$C_6$ alkyl, $C_2$–$C_6$ alkenyl, $C_2$–$C_4$ alkynyl, aryl and aryl-$C_1$–$C_4$ alkyl.

2. A compound according to claim 1, wherein
G is selected from the group consisting of

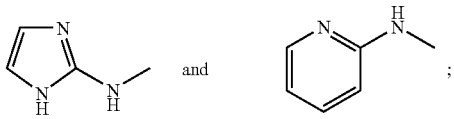

and

R2 is selected from the group consisting of phenyl, thiophene, oxazole, isoxazole, and pyridine, unsubstituted or optionally substituted with one to three substituents independently selected from the group consisting of H, $C_1$–$C_4$ alkyl, $C_1$–$C_4$ alkoxy, OH, halogen and $CF_3$.

3. A pharmaceutical composition comprising a therapeutically effective amount of a compound or a pharmaceutically acceptable salt of the compound or ester of the compound having the formula (I):

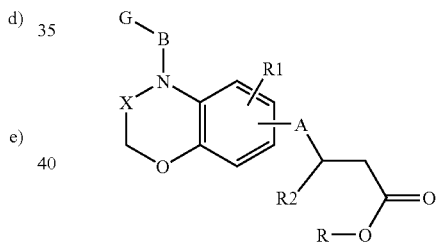

I wherein
G is selected from the group consisting of a) 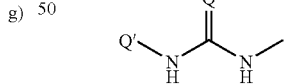

b) 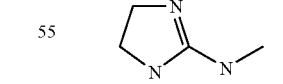

c) 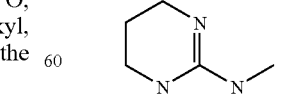

d) 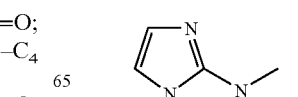

e) 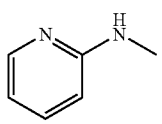

f) 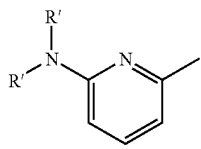

g) 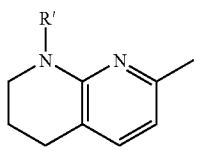

where Q is selected from the group consisting of NH and O, Q' is selected from the group consisting of H, $C_1$–$C_6$ alkyl, phenyl and phenyl-$C_1$–$C_4$-alkyl, and R' is selected from the group consisting of H and $C_1$–$C_4$ alkyl;

B is $(CH_2)_mY$, wherein m=1,2,3 and Y is $CH_2$;

X is selected from the group consisting of $CH_2$ and C=O;

R1 is selected from the group consisting of H, $C_1$–$C_4$ alkyl, $C_1$–$C_4$ alkoxy, OH, halogen, and $CF_3$;

A is selected from the group consisting of $CH_2$, NH, O, and $S(O)_n$ wherein n is zero, 1 or 2;

R2 is selected from the group consisting of phenyl, naphthyl, pyridine, pyrazine, pyridazine, pyrimidine, thiophene, pyrrole, pyrazole, imidazole, oxazole and isoxazole, unsubstituted or optionally substituted with one to three substituents independently selected from the group consisting of H, $C_1$–$C_4$ alkyl, $C_1$–$C_4$ alkoxy, OH, halogen, and $CF_3$; and R is selected from the group consisting of hydrogen, $C_1$–$C_6$ alkyl, $C_2$–$C_6$ alkenyl, $C_2$–$C_4$ alkynyl, aryl and aryl-$C_1$–$C_4$ alkyl.

4. A pharmaceutical composition of claims 3 wherein: G is selected from the group consisting of

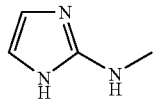 and 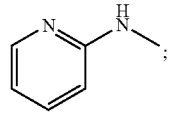

and

R2 is selected from the group consisting of phenyl, thiophene, oxazole, isoxazole, and pyridine, unsubstituted or optionally substituted with one to three substituents independently selected from the group consisting of H, $C_1$–$C_4$ alkyl, $C_1$–$C_4$ alkoxy, OH, halogen and $CF_3$.

* * * * *